(12) United States Patent
Kostrzewski

(10) Patent No.: US 10,499,911 B2
(45) Date of Patent: Dec. 10, 2019

(54) SMALL DIAMETER ENDOSCOPIC STAPLER

(71) Applicant: Covidien LP, Mansfield, MA (US)

(72) Inventor: Stanislaw Kostrzewski, Newtown, CT (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 15/995,902

(22) Filed: Jun. 1, 2018

(65) Prior Publication Data
US 2018/0280025 A1 Oct. 4, 2018

Related U.S. Application Data

(60) Continuation of application No. 15/814,462, filed on Nov. 16, 2017, now Pat. No. 9,987,004, which is a
(Continued)

(51) Int. Cl.
B31D 5/00 (2017.01)
B26D 7/18 (2006.01)
(Continued)

(52) U.S. Cl.
CPC ...... *A61B 17/0684* (2013.01); *A61B 17/0644* (2013.01); *A61B 17/0686* (2013.01);
(Continued)

(58) Field of Classification Search
None
See application file for complete search history.

(56) References Cited

U.S. PATENT DOCUMENTS 1,027,510 A  5/1912  Hiltebrandt
1,506,790 A  9/1924  Shelton, IV
(Continued)

FOREIGN PATENT DOCUMENTS

AU   198654765    9/1986
CA   2773414 A1   11/2012
(Continued)

OTHER PUBLICATIONS

European Extended Search Report dated Jun. 17, 2015 for European Appln. No. EP 14199707.2.
(Continued)

*Primary Examiner* — Hemant Desai
*Assistant Examiner* — Tanzim Imam
(74) *Attorney, Agent, or Firm* — Carter, DeLuca & Farrell LLP

(57) ABSTRACT

A surgical stapler is described herein which includes a shaft portion and a tool assembly supported on a distal end of the shaft portion. The too assembly includes an anvil and a cartridge body which rotatably supports a plurality of staples within notches. At least one firing cam is provided to sequentially to engage and rotate each of the staples to fire the staples from the cartridge body. In embodiments, the cartridge body includes two spaced legs which support two linear rows of staples. Each of the spaced legs of the cartridge body is supported within one of a first and a second cartridge channel. The cartridge channels are fixed to opposite sides of a pivot member which is pivotally supported at a distal end of the shaft portion between the shaft portion and the tool assembly such that translation of the first and second cartridge channels in opposite directions effects articulation of the tool assembly in relation to the shaft portion.

13 Claims, 22 Drawing Sheets

Related U.S. Application Data division of application No. 14/180,578, filed on Feb. 14, 2014, now Pat. No. 9,848,874.

(51) Int. Cl.

| | | |
|---|---|---|
| *B26F 1/20* | (2006.01) | |
| *A61B 17/068* | (2006.01) | |
| *A61B 17/072* | (2006.01) | |
| *A61B 17/064* | (2006.01) | |
| *A61B 17/00* | (2006.01) | |
| *A61B 17/29* | (2006.01) | |

(52) U.S. Cl.
CPC ............ *A61B 17/07207* (2013.01); *A61B 2017/00473* (2013.01); *A61B 2017/07257* (2013.01); *A61B 2017/07271* (2013.01); *A61B 2017/07278* (2013.01); *A61B 2017/2927* (2013.01)

(56) References Cited

U.S. PATENT DOCUMENTS

| | | | |
|---|---|---|---|
| 1,735,703 A | | 11/1929 | Morgan et al. |
| 1,762,445 A | | 6/1930 | Einrich et al. |
| 2,817,339 A | | 12/1957 | Sullivan |
| 3,004,335 A | | 10/1961 | Vaitekunas et al. |
| 3,010,054 A | | 11/1961 | Johnson et al. |
| 3,020,743 A | | 2/1962 | Shelton, IV |
| 3,079,606 A | | 3/1963 | Bobrov et al. |
| 3,490,675 A | | 1/1970 | Green et al. |
| 3,499,591 A | | 3/1970 | Green |
| 3,650,453 A | * | 3/1972 | Smith, Jr. .......... A61B 17/0684 227/136 |
| 3,777,538 A | | 12/1973 | Weatherly et al. |
| 3,882,854 A | | 5/1975 | Hulka et al. |
| 4,027,510 A | | 6/1977 | Hiltebrandt |
| 4,086,926 A | | 5/1978 | Green et al. |
| 4,127,227 A | * | 11/1978 | Green ................ A61B 17/0684 227/19 |
| 4,244,372 A | | 1/1981 | Kapitanov et al. |
| 4,429,695 A | | 2/1984 | Green |
| 4,505,414 A | | 3/1985 | Filipi |
| 4,520,817 A | | 6/1985 | Green |
| 4,589,413 A | | 5/1986 | Malyshev et al. |
| 4,596,351 A | | 6/1986 | Fedotov et al. |
| 4,602,634 A | | 7/1986 | Barkley |
| 4,605,001 A | | 8/1986 | Rothfuss et al. |
| 4,608,981 A | | 9/1986 | Rothfuss et al. |
| 4,610,383 A | | 9/1986 | Rothfuss et al. |
| 4,633,861 A | | 1/1987 | Chow et al. |
| 4,633,874 A | | 1/1987 | Chow et al. |
| 4,671,445 A | | 6/1987 | Barker et al. |
| 4,700,703 A | | 10/1987 | Resnick et al. |
| 4,703,887 A | | 11/1987 | Clanton et al. |
| 4,728,020 A | | 3/1988 | Green et al. |
| 4,752,024 A | | 6/1988 | Green et al. |
| 4,784,137 A | | 11/1988 | Kulik et al. |
| 4,863,088 A | | 9/1989 | Redmond et al. |
| 4,869,415 A | | 9/1989 | Fox |
| 4,892,244 A | | 1/1990 | Fox et al. |
| 4,955,959 A | | 9/1990 | Tompkins et al. |
| 4,978,049 A | | 12/1990 | Green |
| 4,991,764 A | | 2/1991 | Mericle |
| 5,014,899 A | | 5/1991 | Presty et al. |
| 5,031,814 A | | 7/1991 | Tompkins et al. |
| 5,040,715 A | | 8/1991 | Green et al. |
| 5,065,929 A | | 11/1991 | Schulze et al. |
| 5,071,430 A | | 12/1991 | de Salis et al. |
| 5,074,454 A | | 12/1991 | Peters |
| 5,083,695 A | | 1/1992 | Foslien et al. |
| 5,084,057 A | | 1/1992 | Green et al. |
| 5,106,008 A | | 4/1992 | Tompkins et al. |
| 5,111,987 A | | 5/1992 | Moeinzadeh et al. |
| 5,129,570 A | | 7/1992 | Schulze et al. |
| 5,141,144 A | | 8/1992 | Foslien et al. |
| 5,156,315 A | | 10/1992 | Green et al. |
| 5,156,614 A | | 10/1992 | Green et al. |
| 5,163,943 A | | 11/1992 | Mohiuddin et al. |
| 5,170,925 A | | 12/1992 | Madden et al. |
| 5,171,247 A | | 12/1992 | Hughett et al. |
| 5,173,133 A | | 12/1992 | Morin et al. |
| 5,180,092 A | | 1/1993 | Crainich |
| 5,188,274 A | | 2/1993 | Moeinzadeh et al. |
| 5,192,288 A | | 3/1993 | Thompson et al. |
| 5,220,928 A | | 6/1993 | Oddsen et al. |
| 5,221,036 A | | 6/1993 | Takase |
| 5,242,457 A | | 9/1993 | Akopov et al. |
| 5,246,156 A | | 9/1993 | Rothfuss et al. |
| 5,253,793 A | | 10/1993 | Green et al. |
| 5,263,629 A | | 11/1993 | Trumbull et al. |
| RE34,519 E | | 1/1994 | Fox et al. |
| 5,275,323 A | | 1/1994 | Schulze et al. |
| 5,282,807 A | | 2/1994 | Knoepfler |
| 5,282,808 A | | 2/1994 | Kovac et al. |
| 5,289,963 A | | 3/1994 | McGarry et al. |
| 5,307,976 A | | 5/1994 | Olson et al. |
| 5,308,576 A | | 5/1994 | Green et al. |
| 5,312,023 A | | 5/1994 | Green et al. |
| 5,318,221 A | | 6/1994 | Green et al. |
| 5,326,013 A | | 7/1994 | Green et al. |
| 5,328,077 A | | 7/1994 | Lou |
| 5,330,486 A | | 7/1994 | Wilk |
| 5,332,142 A | | 7/1994 | Robinson et al. |
| 5,336,232 A | | 8/1994 | Green et al. |
| 5,344,061 A | | 9/1994 | Crainich |
| 5,352,238 A | | 10/1994 | Green et al. |
| 5,356,064 A | | 10/1994 | Green et al. |
| 5,358,506 A | | 10/1994 | Green et al. |
| 5,364,001 A | | 11/1994 | Bryan |
| 5,364,002 A | | 11/1994 | Green et al. |
| 5,364,003 A | | 11/1994 | Williamson, IV |
| 5,366,133 A | | 11/1994 | Geiste |
| 5,376,095 A | | 12/1994 | Ortiz |
| 5,379,933 A | | 1/1995 | Green et al. |
| 5,381,943 A | | 1/1995 | Allen et al. |
| 5,382,255 A | | 1/1995 | Castro et al. |
| 5,383,880 A | | 1/1995 | Hooven |
| 5,389,098 A | | 2/1995 | Tsuruta et al. |
| 5,395,033 A | | 3/1995 | Byrne et al. |
| 5,395,034 A | | 3/1995 | Allen et al. |
| 5,397,046 A | | 3/1995 | Savage et al. |
| 5,397,324 A | | 3/1995 | Carroll et al. |
| 5,403,312 A | | 4/1995 | Yates et al. |
| 5,405,072 A | | 4/1995 | Zlock et al. |
| 5,407,293 A | | 4/1995 | Crainich |
| 5,413,268 A | | 5/1995 | Green et al. |
| 5,415,334 A | | 5/1995 | Williamson et al. |
| 5,415,335 A | | 5/1995 | Knodell, Jr. |
| 5,417,361 A | | 5/1995 | Williamson, IV |
| 5,423,471 A | | 6/1995 | Mastri et al. |
| 5,425,745 A | | 6/1995 | Green et al. |
| 5,431,322 A | | 7/1995 | Green et al. |
| 5,431,323 A | | 7/1995 | Smith et al. |
| 5,433,721 A | | 7/1995 | Hooven et al. |
| 5,441,193 A | | 8/1995 | Gravener |
| 5,445,304 A | | 8/1995 | Plyley et al. |
| 5,447,265 A | | 9/1995 | Vidal et al. |
| 5,452,837 A | | 9/1995 | Williamson, IV et al. |
| 5,456,401 A | | 10/1995 | Green et al. |
| 5,464,300 A | | 11/1995 | Crainich |
| 5,465,895 A | | 11/1995 | Knodel et al. |
| 5,467,911 A | | 11/1995 | Tsuruta et al. |
| 5,470,007 A | | 11/1995 | Plyley et al. |
| 5,470,010 A | | 11/1995 | Rothfuss et al. |
| 5,472,132 A | | 12/1995 | Savage et al. |
| 5,474,566 A | | 12/1995 | Alesi et al. |
| 5,476,206 A | | 12/1995 | Green et al. |
| 5,478,003 A | | 12/1995 | Green et al. |
| 5,480,089 A | | 1/1996 | Blewett |
| 5,482,197 A | | 1/1996 | Green et al. |
| 5,484,095 A | | 1/1996 | Green et al. |
| 5,484,451 A | * | 1/1996 | Akopov ................ A61B 17/04 227/175.1 |

(56) References Cited

U.S. PATENT DOCUMENTS

| | | |
|---|---|---|
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A | 3/1996 | Green et al. |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,579,107 A | 11/1996 | Wright et al. |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,607,095 A | 3/1997 | Smith et al. |
| 5,615,820 A | 4/1997 | Viola |
| 5,618,291 A | 4/1997 | Thompson et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,630,541 A | 5/1997 | Williamson, IV et al. |
| 5,632,432 A | 5/1997 | Schulze et al. |
| 5,634,584 A | 6/1997 | Okorocha et al. |
| 5,636,780 A | 6/1997 | Green et al. |
| 5,645,209 A | 7/1997 | Green et al. |
| 5,647,526 A | 7/1997 | Green et al. |
| 5,651,491 A | 7/1997 | Heaton et al. |
| 5,653,373 A | 8/1997 | Green et al. |
| 5,653,374 A | 8/1997 | Young et al. |
| 5,653,721 A | 8/1997 | Knodel et al. |
| 5,655,698 A | 8/1997 | Yoon |
| 5,657,921 A | 8/1997 | Young et al. |
| 5,658,300 A | 8/1997 | Bito et al. |
| 5,662,258 A | 9/1997 | Knodel et al. |
| 5,662,259 A | 9/1997 | Yoon |
| 5,662,260 A | 9/1997 | Yoon |
| 5,662,662 A | 9/1997 | Bishop et al. |
| 5,662,666 A | 9/1997 | Onuki et al. |
| 5,665,085 A | 9/1997 | Nardella |
| 5,667,517 A | 9/1997 | Hooven |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,680,981 A | 10/1997 | Mililli et al. |
| 5,680,982 A | 10/1997 | Schulze et al. |
| 5,680,983 A | 10/1997 | Plyley et al. |
| 5,690,269 A | 11/1997 | Bolanos et al. |
| 5,692,668 A | 12/1997 | Schulze et al. |
| 5,697,542 A | 12/1997 | Knodel et al. |
| 5,702,409 A | 12/1997 | Rayburn et al. |
| 5,704,534 A | 1/1998 | Huitema et al. |
| 5,706,997 A | 1/1998 | Green et al. |
| 5,709,334 A | 1/1998 | Sorrentino et al. |
| 5,711,472 A | 1/1998 | Bryan |
| 5,713,505 A | 2/1998 | Huitema |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,110 A | 3/1998 | Vidal et al. |
| 5,732,806 A | 3/1998 | Foshee et al. |
| 5,735,848 A | 4/1998 | Yates et al. |
| 5,743,456 A | 4/1998 | Jones et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,256 A | 6/1998 | Mastri et al. |
| 5,769,303 A | 6/1998 | Knodel et al. |
| 5,769,892 A | 6/1998 | Kingwell |
| 5,772,099 A | 6/1998 | Gravener |
| 5,772,673 A | 6/1998 | Cuny et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,834 A | 7/1998 | Lucey et al. |
| 5,785,232 A | 7/1998 | Vidal et al. |
| 5,797,536 A | 8/1998 | Smith et al. |
| 5,797,537 A | 8/1998 | Oberlin et al. |
| 5,797,538 A | 8/1998 | Heaton et al. |
| 5,810,811 A | 9/1998 | Yates et al. |
| 5,810,855 A | 9/1998 | Rayburn et al. |
| 5,814,055 A | 9/1998 | Knodel et al. |
| 5,814,057 A | 9/1998 | Oi et al. |
| 5,816,471 A | 10/1998 | Plyley et al. |
| 5,817,109 A | 10/1998 | McGarry et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,695 A | 11/1998 | Yoon |
| 5,836,147 A | 11/1998 | Schnipke |
| 5,862,972 A | 1/1999 | Green et al. |
| 5,865,361 A | 2/1999 | Milliman et al. |
| 5,871,135 A | 2/1999 | Williamson, IV et al. |
| 5,873,873 A | 2/1999 | Smith et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,911,352 A | 6/1999 | Racenet et al. |
| 5,911,353 A | 6/1999 | Bolanos et al. |
| 5,918,791 A | 7/1999 | Sorrentino et al. |
| 5,919,198 A | 7/1999 | Graves, Jr. et al. |
| 5,922,001 A | 7/1999 | Yoon |
| 5,931,847 A | 8/1999 | Bittner et al. |
| 5,941,442 A | 8/1999 | Geiste et al. |
| 5,954,259 A | 9/1999 | Viola et al. |
| 5,964,774 A | 10/1999 | McKean et al. |
| 5,980,510 A | 11/1999 | Tsonton et al. |
| 5,988,479 A | 11/1999 | Palmer |
| 6,004,335 A | 12/1999 | Vaitekunas et al. |
| 6,010,054 A | 1/2000 | Johnson et al. |
| 6,032,849 A | 3/2000 | Mastri et al. |
| 6,045,560 A | 4/2000 | McKean et al. |
| 6,063,097 A | 5/2000 | Oi et al. |

(56) References Cited

U.S. PATENT DOCUMENTS

| | | |
|---|---|---|
| 6,079,606 A | 6/2000 | Milliman et al. |
| 6,099,551 A | 8/2000 | Gabbay |
| 6,109,500 A | 8/2000 | Alli et al. |
| 6,131,789 A | 10/2000 | Schulze et al. |
| 6,131,790 A | 10/2000 | Piraka |
| 6,155,473 A | 12/2000 | Tompkins et al. |
| 6,197,017 B1 | 3/2001 | Brock et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,269,977 B1 | 8/2001 | Moore |
| 6,279,809 B1 | 8/2001 | Nicolo |
| 6,315,183 B1 | 11/2001 | Piraka |
| 6,315,184 B1 | 11/2001 | Whitman |
| 6,325,810 B1 | 12/2001 | Hamilton et al. |
| 6,330,965 B1 | 12/2001 | Milkman et al. |
| 6,391,038 B2 | 5/2002 | Vargas et al. |
| 6,398,797 B2 | 6/2002 | Bombard et al. |
| 6,436,097 B1 | 8/2002 | Nardella |
| 6,439,446 B1 | 8/2002 | Perry et al. |
| 6,443,973 B1 | 9/2002 | Whitman |
| 6,463,623 B2 | 10/2002 | Ahn et al. |
| 6,478,804 B2 | 11/2002 | Vargas et al. |
| 6,488,196 B1 | 12/2002 | Fenton, Jr. |
| 6,503,257 B2 | 1/2003 | Grant et al. |
| 6,505,768 B2 | 1/2003 | Whitman |
| 6,544,274 B2 | 4/2003 | Danitz et al. |
| 6,554,844 B2 | 4/2003 | Lee et al. |
| 6,565,554 B1 | 5/2003 | Niemeyer |
| 6,587,750 B2 | 7/2003 | Gerbi et al. |
| 6,592,597 B2 | 7/2003 | Grant et al. |
| 6,594,552 B1 | 7/2003 | Nowlin et al. |
| 6,602,252 B2 | 8/2003 | Mollenauer |
| 6,612,053 B2 | 9/2003 | Liao |
| 6,619,529 B2 | 9/2003 | Green et al. |
| D480,808 S | 10/2003 | Wells et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,731,473 B2 | 5/2004 | Li et al. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,808,262 B2 | 10/2004 | Chapoy et al. |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,877,647 B2 | 4/2005 | Green et al. |
| 6,879,880 B2 | 4/2005 | Nowlin et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |

(56) References Cited

U.S. PATENT DOCUMENTS

| | | |
|---|---|---|
| 7,455,208 B2 | 11/2008 | Wales et al. |
| 7,455,676 B2 | 11/2008 | Holsten et al. |
| 7,458,494 B2 | 12/2008 | Matsutani et al. |
| 7,458,978 B1 | 12/2008 | Bender et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,533,790 B1 | 5/2009 | Knodel et al. |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |
| 7,559,937 B2 | 7/2009 | de la Torre et al. |
| 7,565,993 B2 | 7/2009 | Milliman et al. |
| 7,568,603 B2 | 8/2009 | Shelton, IV et al. |
| 7,568,604 B2 | 8/2009 | Ehrenfels et al. |
| 7,571,845 B2 | 8/2009 | Viola |
| 7,575,144 B2 | 8/2009 | Ortiz et al. |
| 7,584,880 B2 | 9/2009 | Racenet et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,624,903 B2 | 12/2009 | Green et al. |
| 7,631,793 B2 | 12/2009 | Rethy et al. |
| 7,631,794 B2 | 12/2009 | Rethy et al. |
| 7,635,073 B2 | 12/2009 | Heinrich |
| 7,635,074 B2 | 12/2009 | Olson et al. |
| 7,635,373 B2 | 12/2009 | Ortiz |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,658,312 B2 | 2/2010 | Vidal et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,780 B2 | 3/2010 | Shelton, IV et al. |
| 7,673,781 B2 | 3/2010 | Swayze |
| 7,673,782 B2 | 3/2010 | Hess et al. |
| 7,673,783 B2 | 3/2010 | Morgan et al. |
| 7,678,121 B1 | 3/2010 | Knodel |
| 7,681,772 B2 | 3/2010 | Green et al. |
| 7,682,367 B2 | 3/2010 | Shah et al. |
| 7,682,368 B1 | 3/2010 | Bombard et al. |
| 7,690,547 B2 | 4/2010 | Racenet et al. |
| 7,694,865 B2 | 4/2010 | Scirica |
| 7,699,205 B2 | 4/2010 | Ivanko |
| 7,703,653 B2 | 4/2010 | Shah et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,731,072 B2 | 6/2010 | Timm et al. |
| 7,735,703 B2 | 6/2010 | Morgan et al. |
| 7,740,159 B2 | 6/2010 | Shelton, IV et al. |
| 7,740,160 B2 | 6/2010 | Viola |
| 7,743,960 B2 | 6/2010 | Whitman et al. |
| 7,744,628 B2 | 6/2010 | Viola |
| 7,753,245 B2 | 7/2010 | Boudreaux et al. |
| 7,753,248 B2 | 7/2010 | Viola |
| 7,757,924 B2 | 7/2010 | Gerbi et al. |
| 7,757,925 B2 | 7/2010 | Viola et al. |
| 7,762,445 B2 | 7/2010 | Heinrich et al. |
| 7,766,209 B2 | 8/2010 | Baxter, III et al. |
| 7,766,210 B2 | 8/2010 | Shelton, IV et al. |
| 7,766,924 B1 | 8/2010 | Bombard et al. |
| 7,766,928 B2 | 8/2010 | Ezzat et al. |
| 7,770,774 B2 | 8/2010 | Mastri et al. |
| 7,770,775 B2 | 8/2010 | Shelton, IV et al. |
| 7,776,060 B2 | 8/2010 | Mooradian et al. |
| 7,780,055 B2 | 8/2010 | Scirica et al. |
| 7,784,662 B2 | 8/2010 | Wales et al. |
| 7,789,283 B2 | 9/2010 | Shah |
| 7,789,889 B2 | 9/2010 | Zubik et al. |
| 7,793,812 B2 | 9/2010 | Moore et al. |
| 7,793,814 B2 | 9/2010 | Racenet et al. |
| 7,794,475 B2 | 9/2010 | Hess et al. |
| 7,798,385 B2 | 9/2010 | Boyden et al. |
| 7,798,386 B2 | 9/2010 | Schall et al. |
| 7,799,039 B2 | 9/2010 | Shelton, IV et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,815,092 B2 | 10/2010 | Whitman et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,796 B2 | 10/2010 | Blake et al. |
| 7,823,760 B2 | 11/2010 | Zemlok et al. |
| 7,823,761 B2 | 11/2010 | Boyden et al. |
| 7,824,426 B2 | 11/2010 | Racenet et al. |
| 7,828,186 B2 | 11/2010 | Wales |
| 7,828,187 B2 | 11/2010 | Green et al. |
| 7,828,188 B2 | 11/2010 | Jankowski |
| 7,828,189 B2 | 11/2010 | Holsten et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,079 B2 | 11/2010 | Holsten et al. |
| 7,837,081 B2 | 11/2010 | Holsten et al. |
| 7,841,503 B2 | 11/2010 | Sonnenschein et al. |
| 7,845,533 B2 | 12/2010 | Marczyk et al. |

(56) References Cited

U.S. PATENT DOCUMENTS

| | | |
|---|---|---|
| 7,845,534 B2 | 12/2010 | Viola et al. |
| 7,845,535 B2 | 12/2010 | Scircia |
| 7,845,537 B2 | 12/2010 | Shelton, IV et al. |
| 7,845,538 B2 | 12/2010 | Whitman |
| 7,850,703 B2 | 12/2010 | Bombard et al. |
| 7,857,183 B2 | 12/2010 | Shelton, IV |
| 7,857,184 B2 | 12/2010 | Viola |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,861,907 B2 | 1/2011 | Green et al. |
| 7,866,524 B2 | 1/2011 | Krehel |
| 7,866,525 B2 | 1/2011 | Scirica |
| 7,866,526 B2 | 1/2011 | Green et al. |
| 7,866,527 B2 | 1/2011 | Hall et al. |
| 7,866,528 B2 | 1/2011 | Olson et al. |
| 7,870,989 B2 | 1/2011 | Viola et al. |
| 7,886,952 B2 | 2/2011 | Soirica et al. |
| 7,891,532 B2 | 2/2011 | Mastri et al. |
| 7,891,533 B2 | 2/2011 | Green et al. |
| 7,891,534 B2 | 2/2011 | Wenchell et al. |
| 7,896,214 B2 | 3/2011 | Farascioni |
| 7,900,805 B2 | 3/2011 | Shelton, IV et al. |
| 7,901,416 B2 | 3/2011 | Nolan et al. |
| 7,905,380 B2 | 3/2011 | Shelton, IV et al. |
| 7,905,381 B2 | 3/2011 | Baxter, III et al. |
| 7,909,039 B2 | 3/2011 | Hur |
| 7,909,220 B2 | 3/2011 | Viola |
| 7,909,221 B2 | 3/2011 | Viola et al. |
| 7,909,224 B2 | 3/2011 | Prommersberger |
| 7,913,891 B2 | 3/2011 | Doll et al. |
| 7,913,893 B2 | 3/2011 | Mastri et al. |
| 7,914,543 B2 | 3/2011 | Roth et al. |
| 7,918,230 B2 | 4/2011 | Whitman et al. |
| 7,918,276 B2 | 4/2011 | Guignard et al. |
| 7,922,061 B2 | 4/2011 | Shelton, IV et al. |
| 7,922,063 B2 | 4/2011 | Zemlok et al. |
| 7,922,064 B2 | 4/2011 | Boyden et al. |
| 7,926,691 B2 | 4/2011 | Viola et al. |
| 7,926,692 B2 | 4/2011 | Racenet et al. |
| 7,934,628 B2 | 5/2011 | Wenchell et al. |
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 | 1/2012 | Ortiz et al. |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |

(56) References Cited

U.S. PATENT DOCUMENTS

| | | |
|---|---|---|
| 8,210,412 B2 | 7/2012 | Marczyk |
| 8,210,416 B2 | 7/2012 | Milliman et al. |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,261,958 B1 | 9/2012 | Knodel et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,292,146 B2 | 10/2012 | Holsten et al. |
| 8,292,147 B2 | 10/2012 | Viola |
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,469,252 B2 | 6/2013 | Holcomb et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,496,152 B2 | 7/2013 | Viola |
| 8,496,156 B2 | 7/2013 | Sniffin et al. |

(56) References Cited

U.S. PATENT DOCUMENTS

| | | |
|---|---|---|
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,517,241 B2 | 8/2013 | Nicholas et al. |
| 8,517,244 B2 | 8/2013 | Shelton, IV et al. |
| 8,523,043 B2 | 9/2013 | Ullrich et al. |
| 8,540,128 B2 | 9/2013 | Shelton, IV et al. |
| 8,556,151 B2 | 10/2013 | Viola |
| 8,579,176 B2 | 11/2013 | Smith et al. |
| 8,590,762 B2 | 11/2013 | Hess et al. |
| 8,631,990 B1 | 1/2014 | Park et al. |
| 8,631,991 B2 | 1/2014 | Cropper et al. |
| 8,678,263 B2 | 3/2014 | Viola |
| 9,848,874 B2 | 12/2017 | Kostrzewski |
| 9,987,004 B2 | 6/2018 | Kostrzewski |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0103819 A1 | 5/2005 | Racenet et al. |
| 2005/0119669 A1 | 6/2005 | Demmy |
| 2005/0189397 A1 | 9/2005 | Jankowski |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2007/0221700 A1 | 9/2007 | Ortiz et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078800 A1 | 4/2008 | Hess et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169329 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0005808 A1 | 1/2009 | Hess et al. |
| 2009/0036904 A1 | 2/2009 | Milliman et al. |
| 2009/0090763 A1 | 4/2009 | Zemlok et al. |
| 2009/0090766 A1 | 4/2009 | Knodel |
| 2009/0182352 A1 | 7/2009 | Paz et al. |
| 2009/0209946 A1 | 8/2009 | Swayze et al. |
| 2009/0209990 A1 | 8/2009 | Yates et al. |
| 2009/0236395 A1 | 9/2009 | Scirica |
| 2009/0242610 A1 | 10/2009 | Shelton, IV et al. |
| 2009/0254121 A1 | 10/2009 | Newth et al. |
| 2009/0255974 A1 | 10/2009 | Viola |
| 2009/0272787 A1 | 11/2009 | Scirica |
| 2009/0277949 A1 | 11/2009 | Viola et al. |
| 2009/0283568 A1 | 11/2009 | Racenet et al. |
| 2009/0306708 A1 | 12/2009 | Shah |
| 2009/0308907 A1 | 12/2009 | Nalagatla et al. |
| 2010/0012703 A1 | 1/2010 | Calabrese et al. |
| 2010/0012704 A1 | 1/2010 | Tarinelli Racenet et al. |
| 2010/0069942 A1 | 3/2010 | Shelton, IV |
| 2010/0072254 A1 | 3/2010 | Aranyi et al. |
| 2010/0076429 A1 | 3/2010 | Heinrich |
| 2010/0076459 A1 | 3/2010 | Farascioni |
| 2010/0089970 A1 | 4/2010 | Smith et al. |
| 2010/0127041 A1 | 5/2010 | Morgan et al. |
| 2010/0127042 A1 | 5/2010 | Shelton, IV |
| 2010/0133317 A1 | 6/2010 | Shelton, IV et al. |
| 2010/0133318 A1 | 6/2010 | Boudreaux |
| 2010/0147921 A1 | 6/2010 | Olson |
| 2010/0147922 A1 | 6/2010 | Olson |
| 2010/0155453 A1 | 6/2010 | Bombard et al. |
| 2010/0170931 A1 | 7/2010 | Viola |
| 2010/0193566 A1 | 8/2010 | Scheib et al. |
| 2010/0224668 A1 | 9/2010 | Fontayne et al. |
| 2010/0230468 A1 | 9/2010 | Viola |
| 2010/0237130 A1 | 9/2010 | Scirica |
| 2010/0241161 A1 | 9/2010 | Heftman |
| 2010/0243709 A1 | 9/2010 | Hess et al. |
| 2010/0249802 A1 | 9/2010 | May et al. |
| 2010/0252611 A1 | 10/2010 | Ezzat et al. |
| 2010/0252612 A1 | 10/2010 | Viola |
| 2010/0264192 A1 | 10/2010 | Marczyk |
| 2010/0264193 A1 | 10/2010 | Huang et al. |
| 2010/0264194 A1 | 10/2010 | Huang et al. |
| 2010/0294828 A1 | 11/2010 | Bindra et al. |
| 2010/0294829 A1 | 11/2010 | Giordano et al. |
| 2010/0301095 A1 | 12/2010 | Shelton, IV et al. |
| 2010/0305552 A1 | 12/2010 | Shelton, IV et al. |
| 2010/0308100 A1 | 12/2010 | Boudreaux |
| 2010/0320252 A1 | 12/2010 | Viola et al. |
| 2010/0320254 A1 | 12/2010 | Zemlok et al. |
| 2011/0006099 A1 | 1/2011 | Hall et al. |
| 2011/0006101 A1 | 1/2011 | Hall et al. |
| 2011/0006103 A1 | 1/2011 | Laurent et al. |
| 2011/0011914 A1 | 1/2011 | Baxter, III et al. |
| 2011/0011915 A1 | 1/2011 | Shelton, IV |
| 2011/0017801 A1 | 1/2011 | Zemlok et al. |
| 2011/0024477 A1 | 2/2011 | Hall |
| 2011/0024478 A1 | 2/2011 | Shelton, IV |
| 2011/0036887 A1 | 2/2011 | Zemlok et al. |
| 2011/0036888 A1 | 2/2011 | Pribanic et al. |
| 2011/0036890 A1 | 2/2011 | Ma |
| 2011/0036891 A1 | 2/2011 | Zemlok et al. |
| 2011/0036892 A1 | 2/2011 | Marczyk et al. |
| 2011/0036895 A1 | 2/2011 | Marczyk et al. |
| 2011/0042439 A1 | 2/2011 | Johnson et al. |
| 2011/0042441 A1 | 2/2011 | Shelton, IV et al. |
| 2011/0062213 A1 | 3/2011 | Scirica et al. |
| 2011/0068145 A1 | 3/2011 | Bedi et al. |
| 2011/0068148 A1 | 3/2011 | Hall et al. |
| 2011/0084114 A1 | 4/2011 | Marczyk et al. |
| 2011/0084115 A1 | 4/2011 | Bedi et al. |
| 2011/0087276 A1 | 4/2011 | Bedi et al. |
| 2011/0089221 A1 | 4/2011 | Masiakos et al. |
| 2011/0095067 A1 | 4/2011 | Ohdaira |
| 2011/0101067 A1 | 5/2011 | Johnson et al. |
| 2011/0101069 A1 | 5/2011 | Bombard et al. |
| 2011/0108603 A1 | 5/2011 | Racenet et al. |
| 2011/0114702 A1 | 5/2011 | Farascioni |
| 2011/0121049 A1 | 5/2011 | Malinouskas et al. |
| 2011/0132961 A1 | 6/2011 | Whitman et al. |
| 2011/0132963 A1 | 6/2011 | Giordano et al. |
| 2011/0132964 A1 | 6/2011 | Weisenburgh, II et al. |
| 2011/0132965 A1 | 6/2011 | Moore et al. |
| 2011/0139851 A1 | 6/2011 | McCuen |
| 2011/0144640 A1 | 6/2011 | Heinrich et al. |
| 2011/0147433 A1 | 6/2011 | Shelton, IV et al. |
| 2011/0147434 A1 | 6/2011 | Hueil et al. |
| 2011/0155781 A1 | 6/2011 | Swensgard et al. |
| 2011/0155784 A1 | 6/2011 | Shelton, IV et al. |
| 2011/0155786 A1 | 6/2011 | Shelton, IV |
| 2011/0155787 A1 | 6/2011 | Baxter, III et al. |

(56) References Cited

U.S. PATENT DOCUMENTS

| | | |
|---|---|---|
| 2011/0155788 A1 | 6/2011 | Hillstead et al. |
| 2011/0163146 A1 | 7/2011 | Ortiz et al. |
| 2011/0163147 A1 | 7/2011 | Laurent et al. |
| 2011/0163149 A1 | 7/2011 | Viola |
| 2011/0163150 A1 | 7/2011 | Farascioni |
| 2011/0168757 A1 | 7/2011 | Viola et al. |
| 2011/0168760 A1 | 7/2011 | Viola et al. |
| 2011/0174862 A1 | 7/2011 | Shelton, IV et al. |
| 2011/0174863 A1 | 7/2011 | Shelton, IV et al. |
| 2011/0180585 A1 | 7/2011 | Czemik et al. |
| 2011/0186614 A1 | 8/2011 | Kasvikis |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0198385 A1 | 8/2011 | Whitman et al. |
| 2011/0198386 A1 | 8/2011 | Viola |
| 2011/0204119 A1 | 8/2011 | McCuen |
| 2011/0204120 A1 | 8/2011 | Crainich |
| 2011/0210157 A1 | 9/2011 | Knodel et al. |
| 2011/0215132 A1 | 9/2011 | Aranyi et al. |
| 2011/0215133 A1 | 9/2011 | Aranyi |
| 2011/0226837 A1 | 9/2011 | Baxter, III et al. |
| 2011/0233258 A1 | 9/2011 | Boudreaux |
| 2011/0233259 A1 | 9/2011 | Olson |
| 2011/0240713 A1 | 10/2011 | Scirica et al. |
| 2011/0240714 A1 | 10/2011 | Whitman et al. |
| 2011/0253765 A1 | 10/2011 | Nicholas et al. |
| 2011/0257679 A1 | 10/2011 | Ishitsuki et al. |
| 2011/0272448 A1 | 11/2011 | Scirica et al. |
| 2011/0278343 A1 | 11/2011 | Knodel et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0290855 A1 | 12/2011 | Moore et al. |
| 2011/0290856 A1 | 12/2011 | Shelton, IV et al. |
| 2011/0309127 A1 | 12/2011 | Knodel et al. |
| 2011/0309128 A1 | 12/2011 | Okoniewski |
| 2012/0012636 A1 | 1/2012 | Beckman et al. |
| 2012/0016362 A1 | 1/2012 | Heinrich et al. |
| 2012/0037683 A1 | 2/2012 | Lee |
| 2012/0053406 A1 | 3/2012 | Conlon et al. |
| 2012/0055972 A1 | 3/2012 | Marczyk |
| 2012/0061446 A1 | 3/2012 | Knodel et al. |
| 2012/0061450 A1 | 3/2012 | Kostrzewski |
| 2012/0071866 A1 | 3/2012 | Kerr et al. |
| 2012/0074196 A1 | 3/2012 | Shelton, IV et al. |
| 2012/0074200 A1 | 3/2012 | Schmid et al. |
| 2012/0074201 A1 | 3/2012 | Baxter, III et al. |
| 2012/0080474 A1 | 4/2012 | Farascioni |
| 2012/0080475 A1 | 4/2012 | Smith et al. |
| 2012/0080476 A1 | 4/2012 | Whitman et al. |
| 2012/0080477 A1 | 4/2012 | Leimbach et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080494 A1 | 4/2012 | Thompson et al. |
| 2012/0080495 A1 | 4/2012 | Holcomb et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0091183 A1 | 4/2012 | Manoux et al. |
| 2012/0100200 A1 | 4/2012 | Belcheva et al. |
| 2012/0138659 A1 | 6/2012 | Marczyk et al. |
| 2012/0138660 A1 | 6/2012 | Shelton, IV |
| 2012/0150176 A1 | 6/2012 | Weizman |
| 2012/0160892 A1 | 6/2012 | Scirica |
| 2012/0168484 A1 | 7/2012 | Scirica et al. |
| 2012/0168485 A1 | 7/2012 | Marczyk et al. |
| 2012/0168486 A1 | 7/2012 | Ingmanson et al. |
| 2012/0175399 A1 | 7/2012 | Shelton et al. |
| 2012/0181322 A1 | 7/2012 | Whitman et al. |
| 2012/0187179 A1 | 7/2012 | Gleiman |
| 2012/0193390 A1 | 8/2012 | Racenet et al. |
| 2012/0193394 A1 | 8/2012 | Holcomb et al. |
| 2012/0193399 A1 | 8/2012 | Holcomb et al. |
| 2012/0199630 A1 | 8/2012 | Shelton, IV |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0205421 A1 | 8/2012 | Shelton, IV |
| 2012/0211542 A1 | 8/2012 | Racenet |
| 2012/0217282 A1 | 8/2012 | Beetel |
| 2012/0217283 A1 | 8/2012 | Cohen et al. |
| 2012/0223121 A1 | 9/2012 | Viola et al. |
| 2012/0223122 A1 | 9/2012 | Roy |
| 2012/0223123 A1 | 9/2012 | Baxter, III et al. |
| 2012/0228358 A1 | 9/2012 | Zemlok et al. |
| 2012/0234893 A1 | 9/2012 | Schuckmann et al. |
| 2012/0234895 A1 | 9/2012 | O'Connor et al. |
| 2012/0234896 A1 | 9/2012 | Ellerhorst et al. |
| 2012/0234897 A1 | 9/2012 | Shelton, IV et al. |
| 2012/0234899 A1 | 9/2012 | Scheib et al. |
| 2012/0234900 A1 | 9/2012 | Swayze |
| 2012/0239009 A1 | 9/2012 | Mollere et al. |
| 2012/0241491 A1 | 9/2012 | Aldridge et al. |
| 2012/0241492 A1 | 9/2012 | Shelton, IV et al. |
| 2012/0241493 A1 | 9/2012 | Baxter, III et al. |
| 2012/0241496 A1 | 9/2012 | Mandakolathur Vasudevan et al. |
| 2012/0241497 A1 | 9/2012 | Mandakolathur Vasudevan et al. |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241504 A1 | 9/2012 | Soltz et al. |
| 2012/0241505 A1 | 9/2012 | Alexander, III et al. |
| 2012/0248169 A1 | 10/2012 | Widenhouse et al. |
| 2012/0248170 A1 | 10/2012 | Marczyk |
| 2012/0255985 A1 | 10/2012 | Ma et al. |
| 2012/0255986 A1 | 10/2012 | Petty et al. |
| 2012/0273546 A1 | 11/2012 | Whitman et al. |
| 2012/0273547 A1 | 11/2012 | Hodgkinson et al. |
| 2012/0273550 A1 | 11/2012 | Scirica |
| 2012/0286019 A1 | 11/2012 | Hueil et al. |
| 2012/0286020 A1 | 11/2012 | Smith et al. |
| 2012/0286021 A1 | 11/2012 | Kostrzewski |
| 2012/0286022 A1 | 11/2012 | Olson et al. |
| 2012/0292369 A1 | 11/2012 | Munro, III et al. |
| 2012/0298719 A1 | 11/2012 | Shelton, IV et al. |
| 2012/0298722 A1 | 11/2012 | Hess et al. |
| 2012/0312858 A1 | 12/2012 | Patankar et al. |
| 2012/0312859 A1 | 12/2012 | Gupta et al. |
| 2012/0312860 A1 | 12/2012 | Ming et al. |
| 2012/0312861 A1 | 12/2012 | Gurumurthy et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0318846 A1 | 12/2012 | Wazer et al. |
| 2012/0318847 A1 | 12/2012 | Zemlok et al. |
| 2012/0325891 A1 | 12/2012 | Farascioni et al. |
| 2012/0325893 A1 | 12/2012 | Pastorelli et al. |
| 2013/0001270 A1 | 1/2013 | Kostrzewski |
| 2013/0008937 A1 | 1/2013 | Viola |
| 2013/0012983 A1 | 1/2013 | Kleyman |
| 2013/0015231 A1 | 1/2013 | Kostrzewski |
| 2013/0015233 A1 | 1/2013 | Viola |

(56) References Cited

U.S. PATENT DOCUMENTS

| | | |
|---|---|---|
| 2013/0020374 A1 | 1/2013 | Ivanko |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0030428 A1 | 1/2013 | Worrell et al. |
| 2013/0032626 A1 | 2/2013 | Smith et al. |
| 2013/0032627 A1 | 2/2013 | Viola |
| 2013/0032629 A1 | 2/2013 | Viola |
| 2013/0037594 A1 | 2/2013 | Dhakad et al. |
| 2013/0037595 A1 | 2/2013 | Gupta et al. |
| 2013/0037596 A1 | 2/2013 | Bear et al. |
| 2013/0037597 A1 | 2/2013 | Katre et al. |
| 2013/0037598 A1 | 2/2013 | Marczyk |
| 2013/0037600 A1 | 2/2013 | (Prommersberger) Stopek et al. |
| 2013/0041406 A1 | 2/2013 | Bear et al. |
| 2013/0048697 A1 | 2/2013 | Shelton, IV et al. |
| 2013/0056518 A1 | 3/2013 | Swensgard |
| 2013/0056520 A1 | 3/2013 | Swensgard |
| 2013/0056521 A1 | 3/2013 | Swensgard |
| 2013/0056522 A1 | 3/2013 | Swensgard |
| 2013/0062391 A1 | 3/2013 | Boudreaux et al. |
| 2013/0062393 A1 | 3/2013 | Bruewer et al. |
| 2013/0062394 A1 | 3/2013 | Smith et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0068820 A1 | 3/2013 | Miller et al. |
| 2013/0068821 A1 | 3/2013 | Huitema et al. |
| 2013/0075443 A1 | 3/2013 | Giordano et al. |
| 2013/0075444 A1 | 3/2013 | Cappola et al. |
| 2013/0075445 A1 | 3/2013 | Balek et al. |
| 2013/0075446 A1 | 3/2013 | Wang et al. |
| 2013/0075447 A1 | 3/2013 | Weisenburgh, II et al. |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0075451 A1 | 3/2013 | Balek et al. |
| 2013/0082086 A1 | 4/2013 | Hueil et al. |
| 2013/0087597 A1 | 4/2013 | Shelton, IV et al. |
| 2013/0087599 A1 | 4/2013 | Krumanaker et al. |
| 2013/0087600 A1 | 4/2013 | Scirica |
| 2013/0087601 A1 | 4/2013 | Farascioni |
| 2013/0087602 A1 | 4/2013 | Olson et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098966 A1 | 4/2013 | Kostrzewski et al. |
| 2013/0098968 A1 | 4/2013 | Aranyi |
| 2013/0098969 A1 | 4/2013 | Scirica et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105549 A1 | 5/2013 | Holsten et al. |
| 2013/0105550 A1 | 5/2013 | Zemlok et al. |
| 2013/0105552 A1 | 5/2013 | Weir et al. |
| 2013/0105553 A1 | 5/2013 | (Tarinelli) Racenet et al. |
| 2013/0112729 A1 | 5/2013 | Beardsley et al. |
| 2013/0112730 A1 | 5/2013 | Whitman et al. |
| 2013/0112731 A1 | 5/2013 | Hodgkinson |
| 2013/0112732 A1 | 5/2013 | Aranyi et al. |
| 2013/0112733 A1 | 5/2013 | Aranyi et al. |
| 2013/0112734 A1 | 5/2013 | Aranyi et al. |
| 2013/0119109 A1 | 5/2013 | Farascioni et al. |
| 2013/0119110 A1 | 5/2013 | Scirica |
| 2013/0126581 A1 | 5/2013 | Yates et al. |
| 2013/0126582 A1 | 5/2013 | Shelton, IV et al. |
| 2013/0126583 A1 | 5/2013 | Hueil et al. |
| 2013/0126586 A1 | 5/2013 | Zhang et al. |
| 2013/0140342 A1 | 6/2013 | Milliman et al. |
| 2013/0140343 A1 | 6/2013 | Knodel |
| 2013/0144333 A1 | 6/2013 | Viola |
| 2013/0248577 A1 | 9/2013 | Leimbach et al. |
| 2013/0334278 A1 | 12/2013 | Kerr et al. |
| 2015/0173756 A1 | 6/2015 | Baxter, III et al. |

FOREIGN PATENT DOCUMENTS

| | | |
|---|---|---|
| DE | 2744824 A1 | 4/1978 |
| DE | 2903159 A1 | 7/1980 |
| DE | 3114135 A1 | 10/1982 |
| DE | 4213426 A1 | 10/1992 |
| DE | 4300307 A1 | 7/1994 |
| EP | 0273469 A2 | 7/1977 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A3 | 3/1993 |
| EP | 0536903 A2 | 4/1993 |
| EP | 0537572 A2 | 4/1993 |
| EP | 0539762 A1 | 5/1993 |
| EP | 0545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593220 A2 | 4/1994 |
| EP | 0593920 A1 | 4/1994 |
| EP | 0705571 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0760230 A1 | 3/1997 |
| EP | 2039308 A2 | 3/2009 |
| EP | 2090253 A2 | 8/2009 |
| EP | 2090254 A1 | 8/2009 |
| EP | 2583630 A2 | 4/2013 |
| EP | 2586382 A2 | 5/2013 |
| FR | 2542188 A1 | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| JP | 2008093420 | 4/2008 |
| JP | 2010537792 A | 12/2010 |
| SU | 659146 A1 | 4/1979 |
| SU | 728848 A1 | 4/1980 |
| SU | 980703 A1 | 12/1982 |
| SU | 990220 A1 | 1/1983 |
| WO | 8302247 A1 | 7/1983 |
| WO | 8910094 A1 | 11/1989 |

(56) References Cited

FOREIGN PATENT DOCUMENTS

| | | |
|---|---|---|
| WO | 9210976 A1 | 7/1992 |
| WO | 9308754 A1 | 5/1993 |
| WO | 9314706 A1 | 8/1993 |
| WO | 0170119 A1 | 9/2001 |
| WO | 2004032760 A2 | 4/2004 |
| WO | 2013151820 A1 | 10/2013 |

OTHER PUBLICATIONS

Extended European Search Report corresponding to European Application No. 14 16 6223.9, dated Jun. 3, 2014; 6 pages.
European Search Report dated Apr. 10, 2017, issued in EP Application No. 16200194.
Australian Office Action dated Dec. 6, 2019, issued in Australian Appln. No. 2014259543.
Japanese Office Action dated Oct. 17, 2018 issued in JP Application No. 2014249857.

* cited by examiner

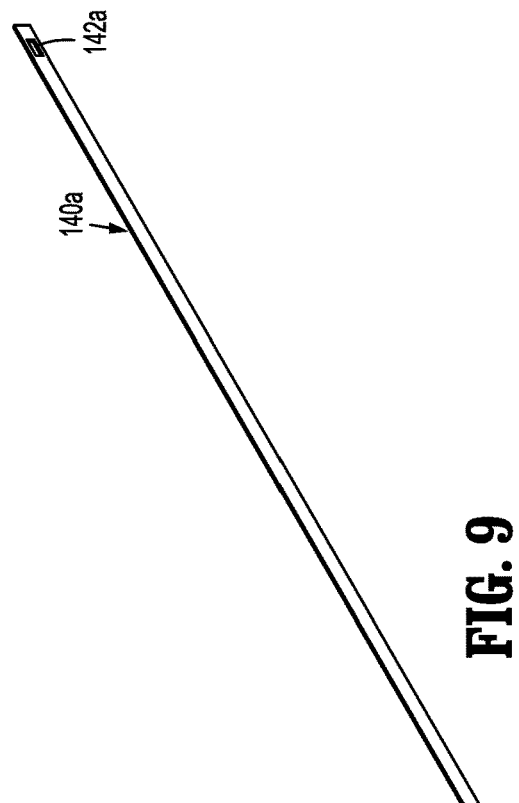
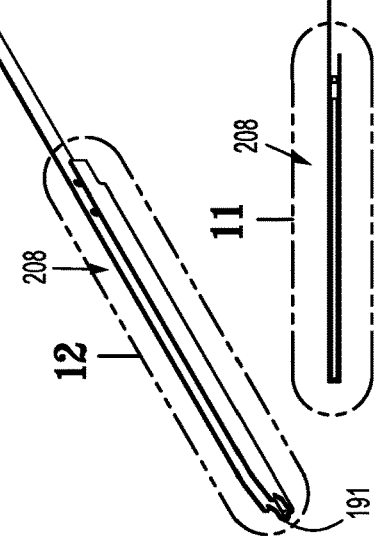
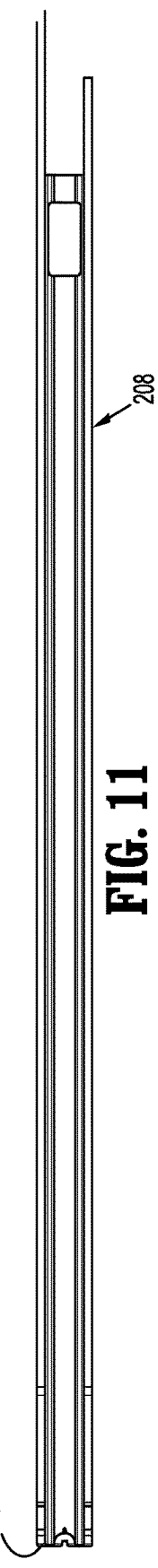
FIG. 9
FIG. 10
FIG. 11

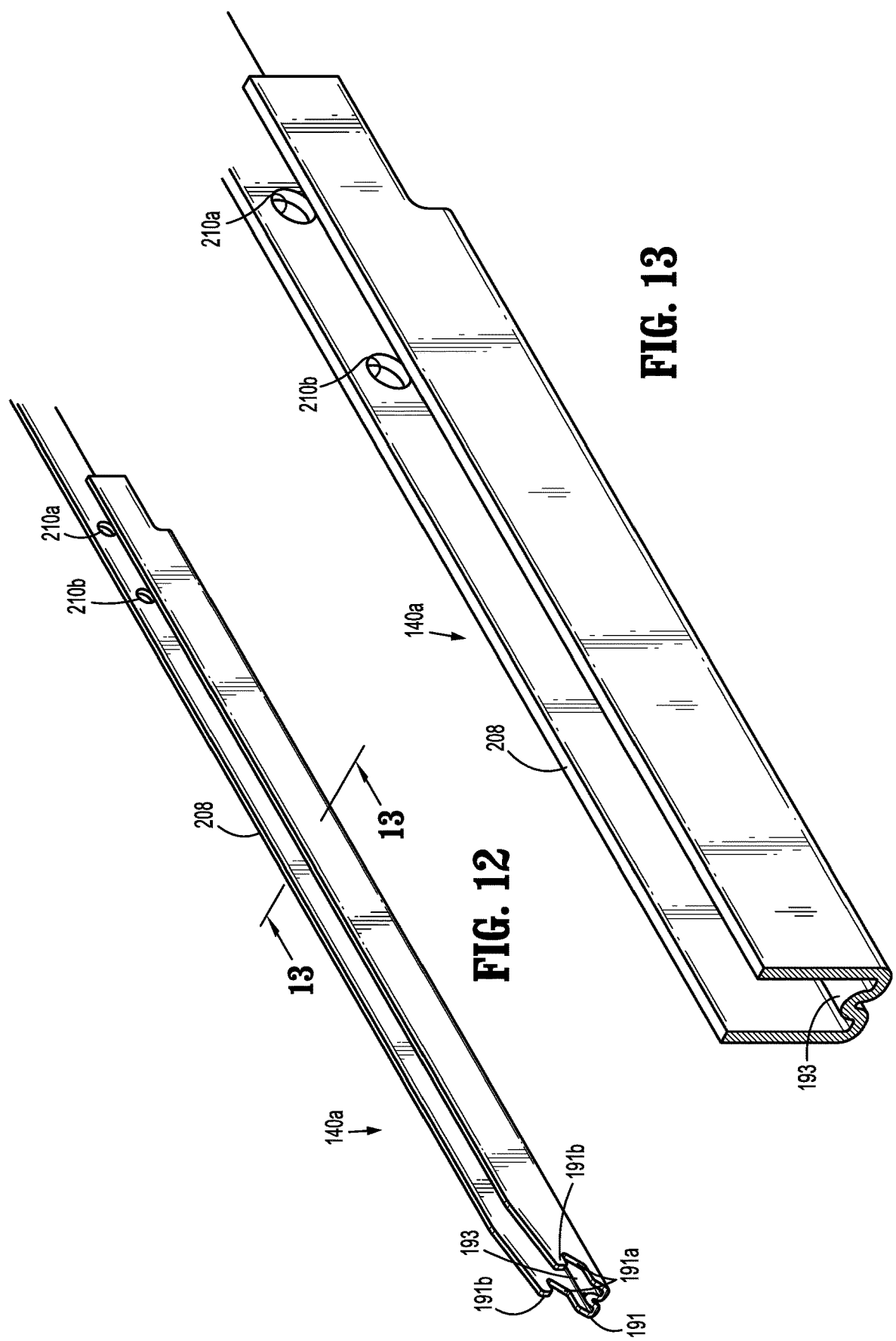

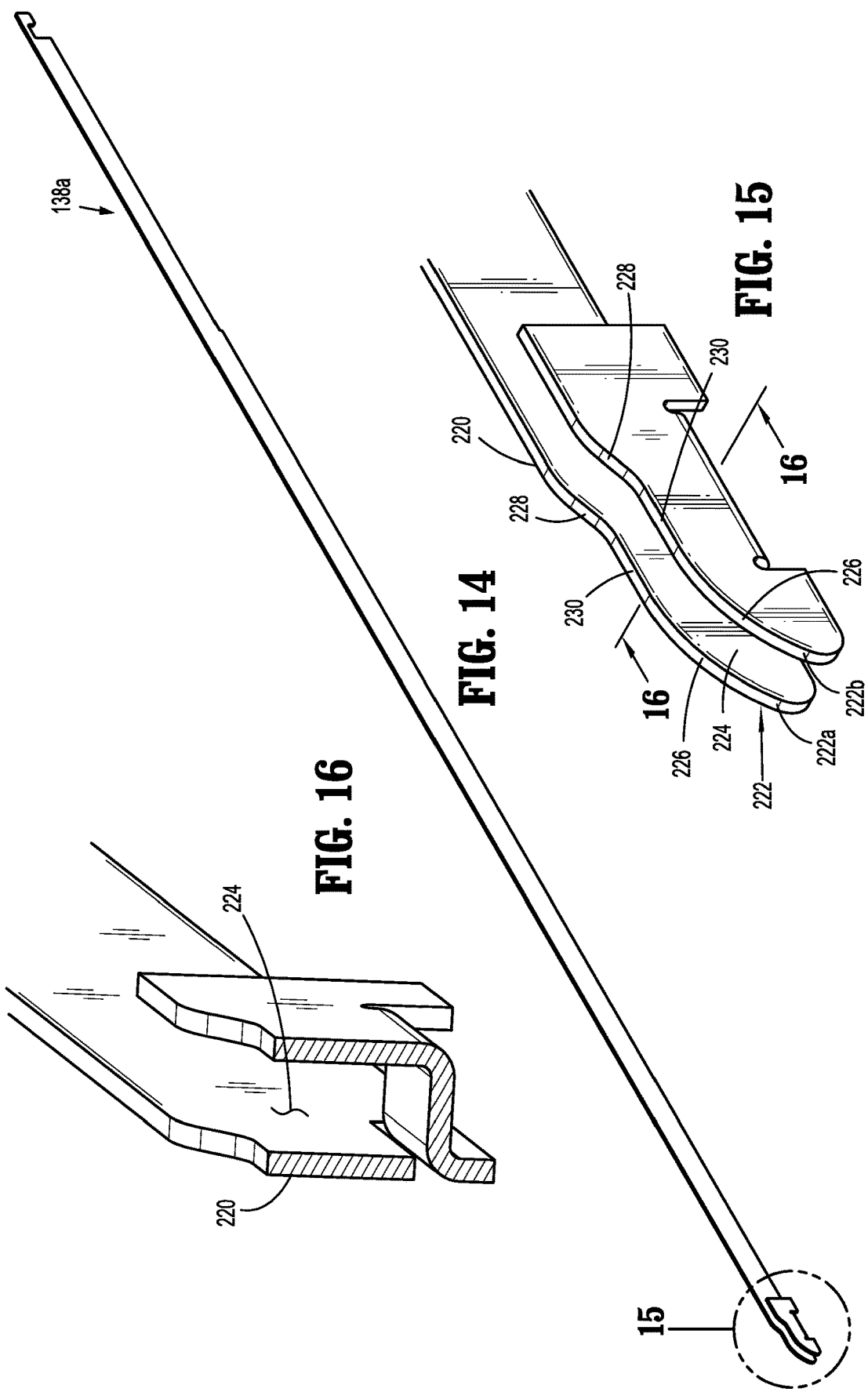

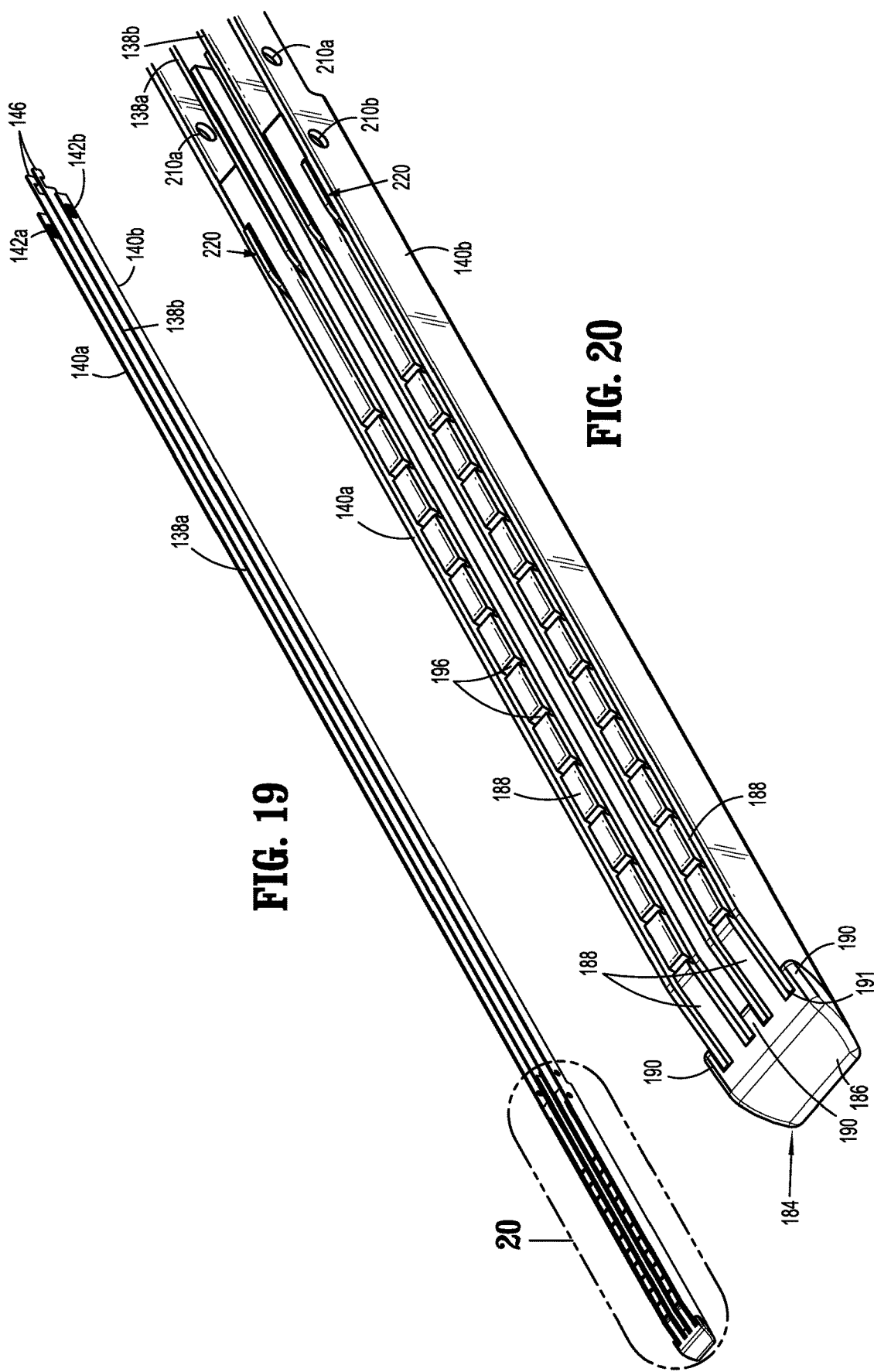

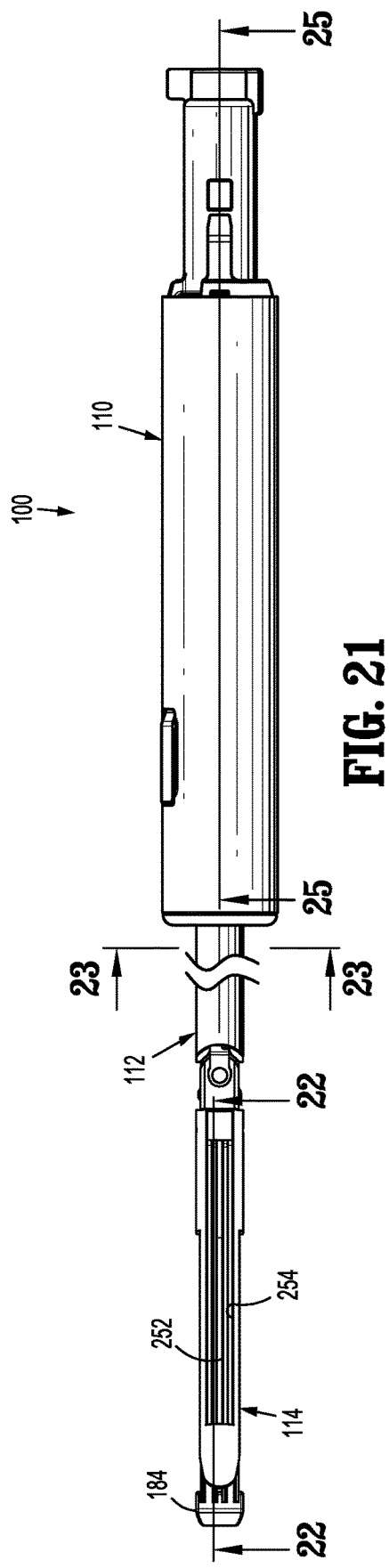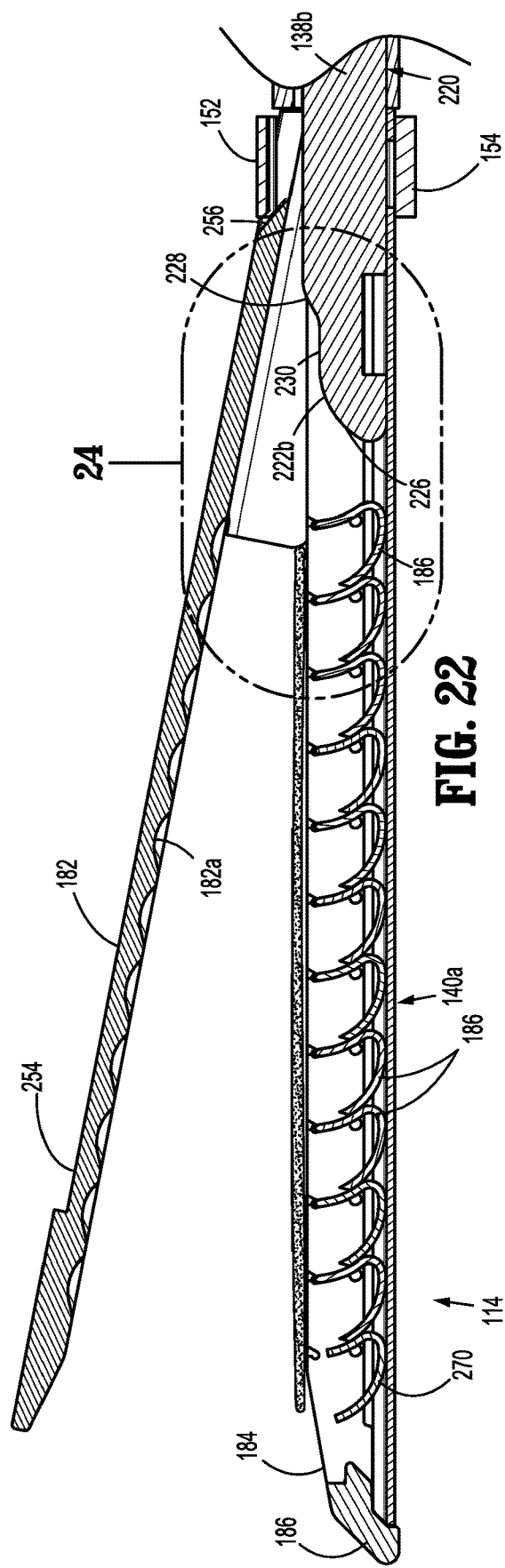

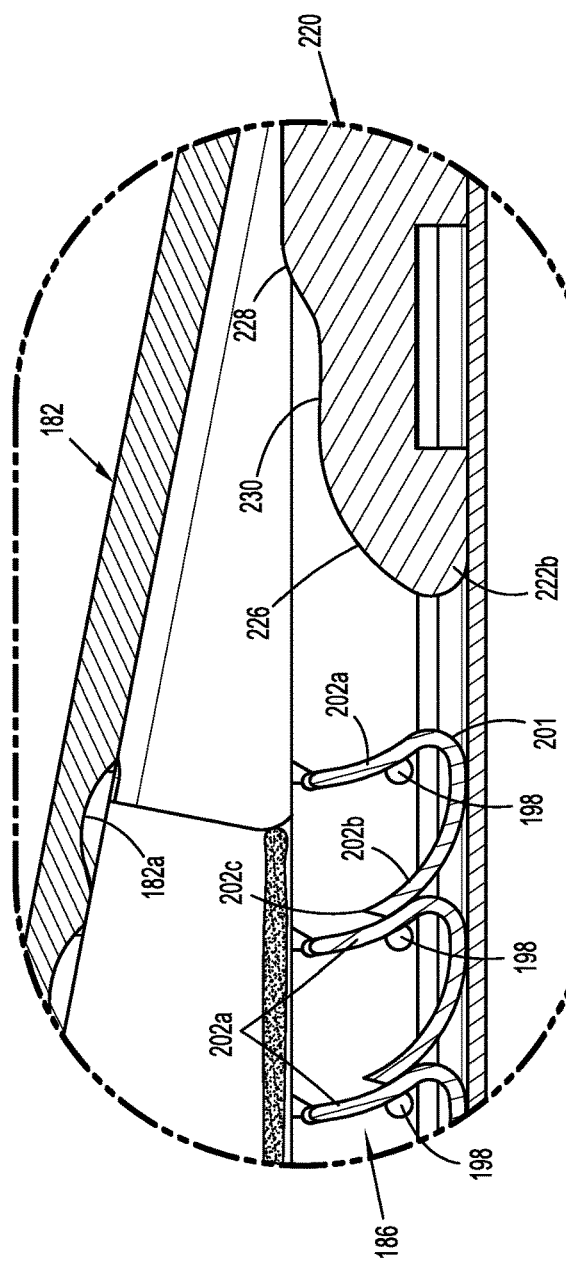
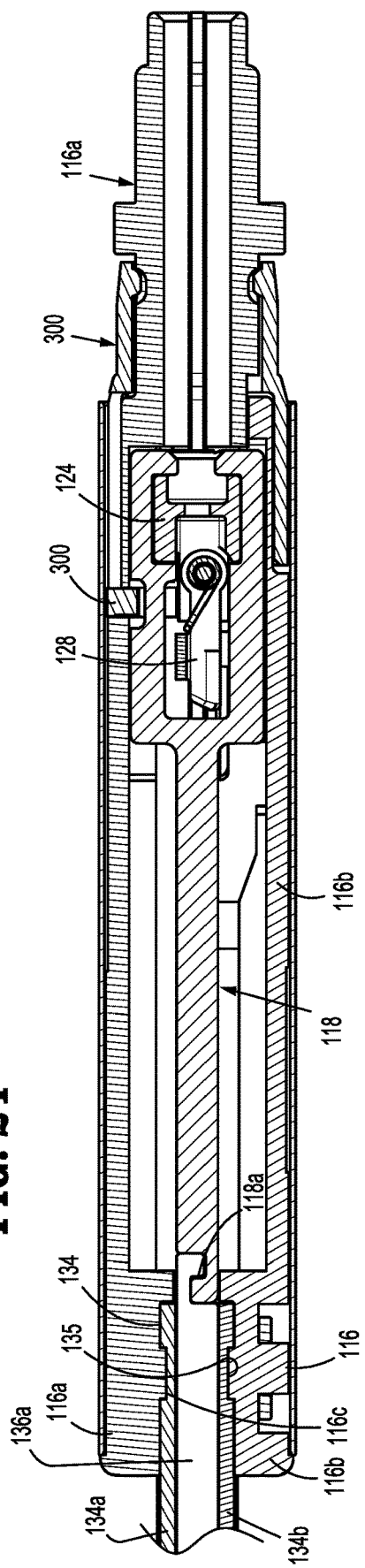
FIG. 24
FIG. 25

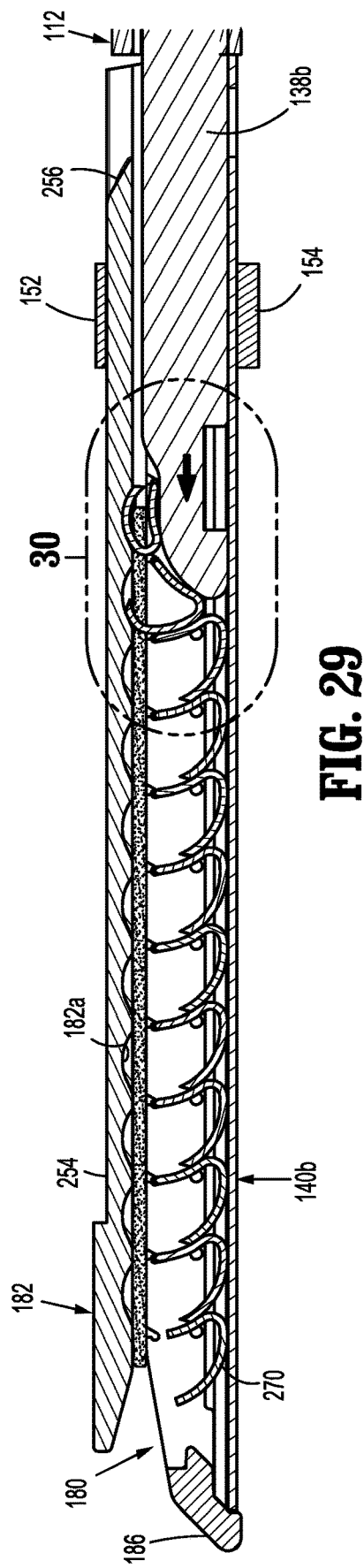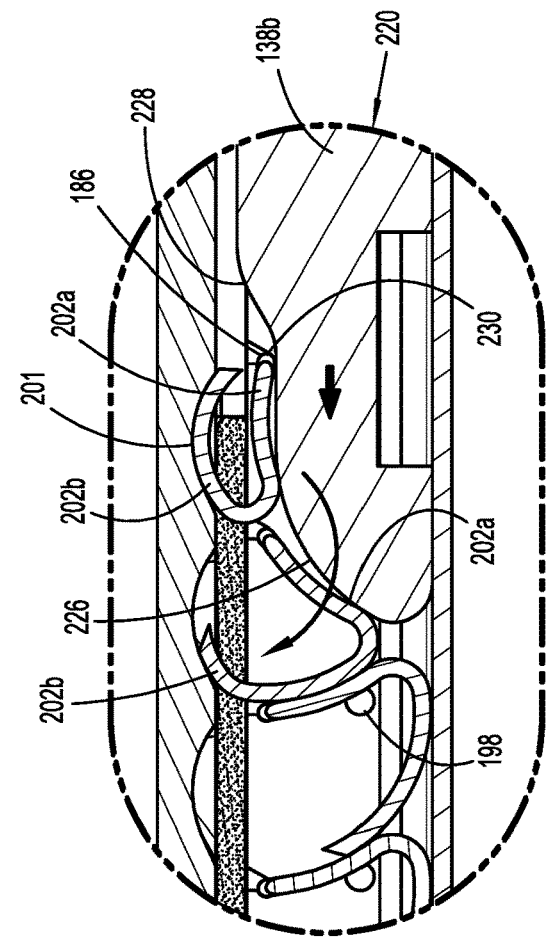
FIG. 29
FIG. 30

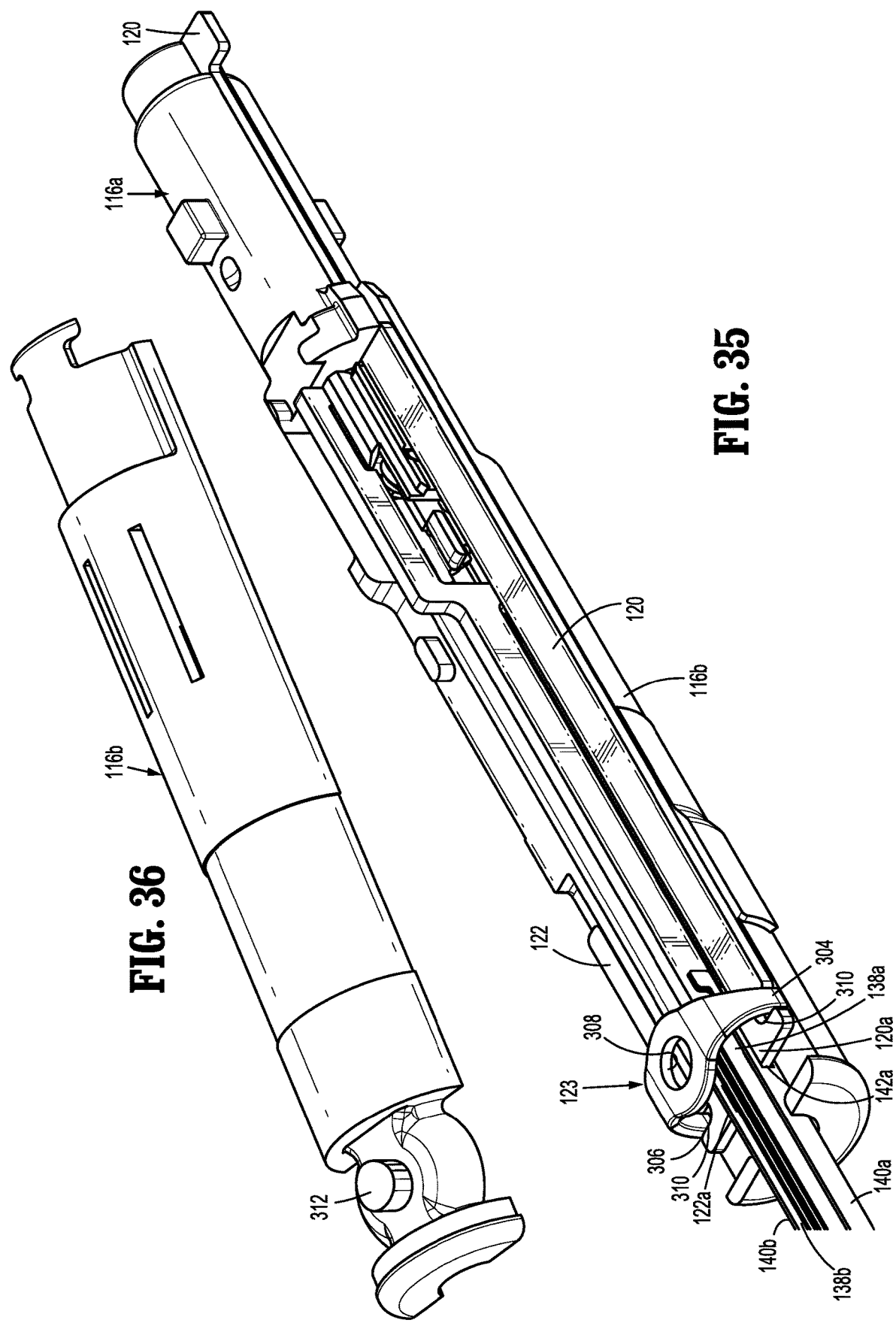

SMALL DIAMETER ENDOSCOPIC STAPLER

CROSS-REFERENCE TO RELATED APPLICATIONS

This application is a continuation of U.S. patent application Ser. No. 15/814,462 filed Nov. 16, 2017, which is a divisional of U.S. patent application Ser. No. 14/180,578 filed Feb. 14, 2014, now U.S. Pat. No. 9,848,874, the disclosures of each of the above-identified applications are hereby incorporated by reference in their entirety.

BACKGROUND

Technical Field

The present disclosure relates to surgical staplers, and more particularly, to surgical staplers for laparoscopic or endoscopic use.

Background

Surgical staplers for stapling tissue during a variety of different surgical procedures are well known in the art. Such staplers typically include a knife to effect the simultaneous dissection and suturing tissue. When compared to applying manually threaded sutures, the use of staplers to suture tissue has increased the speed of the suturing process and thus, minimized patient trauma.

Surgical staplers suitable for use in open-type surgical procedures and laparoscopic or endoscopic (hereinafter "endoscopic") surgical procedures are well known. In an endoscopic surgical procedure, a surgical stapler is inserted through a small incision in the skin or through a cannula to access a surgical site. Due to the complexity of known surgical staplers as well as the staple size requirements or known staple forming apparatus, a continued need exists for small diameter staples suitable for insertion through a small diameter cannula, e.g., a 5 mm cannula.

SUMMARY

A surgical stapler is described which includes a shaft portion and a tool assembly supported on a distal end of the shaft portion. The tool assembly includes an anvil and a cartridge assembly. The cartridge assembly includes a cartridge body having at least one leg defining a plurality of notches and a plurality of staples. Each of the plurality staples has a backspan and a pair of curved legs connected to the backspan. The backspan of each of the plurality of staples is rotatably supported within a respective notch of the plurality of notches. At least one firing cam includes a distal end defining a cam member which is movable within the tool assembly into sequential engagement with each of the plurality of staples. Engagement between the cam member and a staple of the plurality of staples effects rotational movement of the staple into the anvil member to fire the staple from the cartridge body.

In certain embodiments, each notch of the plurality of notches includes a cylindrical slot and the backspan of each of the plurality of staples is positioned within the cylindrical slot in a snap-fit manner.

In embodiments, the cam member of the at least one firing cam includes a first cam surface and a second cam surface. The first cam surface is positioned to engage one curved leg of the pair of curved legs of each of the plurality of staples and the second cam surface is positioned to engage the other curved leg of the pair of curved legs of each of the plurality of staples.

In certain embodiments, the at least one leg of the cartridge body includes two spaced legs and the plurality of notches are spaced axially along each of the two spaced legs. Each of the plurality of notches rotatably supports one staple of the plurality of staples.

In embodiments, the surgical stapler includes first and second cartridge channels having a distal end defining a U-shaped member and the two spaced legs of the cartridge body and secured within the U-shaped members.

In certain embodiments, the at least one firing cam includes first and second firing cams. Each of the cam members of the first and second firing cams has a U-shape and is positioned about one of the two spaced legs of the cartridge body and within the U-shaped member of one of the first and second cartridge channels.

In an embodiment, the surgical stapler includes a pivot member pivotably secured to the distal end of the shaft portion and fixedly secured to each of the first and second cartridge channels.

In certain embodiments, the surgical stapler includes a first articulation link having a distal end secured to a proximal end of the first cartridge channel and a second articulation link secured to a proximal end of the second cartridge channel. The first and second articulation links is axially movable to effect axial movement of the first and second cartridge channels in relation to each other to pivot the pivot member in relation to the shaft portion.

In embodiments, the surgical stapler includes a pivotal articulation member interconnecting the first articulation link to the second articulation link such that movement of the first articulation link in one direction effects movement of the second articulation link in an opposite direction.

In certain embodiments, each of the pair of curved legs of the plurality of staples is U-shaped and includes a proximal leg portion connected to the backspan and a distal leg portion having a tapered tip.

In embodiments, the at least one leg of the cartridge body includes a plurality of dimples wherein each of the dimples is positioned to engage the proximal leg portion of one of the plurality of staples to stabilize the plurality of staples on the cartridge body.

In certain embodiments, the plurality of staples are supported along the cartridge body such that the proximal leg portion of each staple of the plurality of staples is positioned to guide the distal leg portion of a proximally positioned adjacent staple of the plurality of staples as the proximally positioned adjacent staple is fired from the cartridge body.

In certain embodiments, the distal-most staple of the plurality of staples is a dummy staple which is positioned to guide an adjacent proximal staple during firing but is not fired.

A surgical stapler is also described which includes a shaft portion having a proximal end and a distal end and first and second cartridge channels extending through the shaft portion. Each of the first and second cartridge channels has a distal end defining a U-shaped member. A pivot member is pivotally coupled to the distal end of the shaft portion and fixedly coupled to the first cartridge channel by a first post and fixedly coupled to the second cartridge channel by a second post. A tool assembly includes an anvil and a cartridge assembly. The cartridge assembly includes a cartridge body and a plurality of staples. The cartridge body has a first leg supported in the U-shaped member of the first cartridge channel and a second leg supported in the U-shaped member of the second cartridge channel, wherein the first and second cartridge channels are movable axially in opposite directions to pivot the pivot member in relation to the shaft portion and effect articulation of the tool assembly.

In embodiments, the surgical further includes a first articulation link having a distal end secured to a proximal end of the first cartridge channel and a second articulation link secured to a proximal end of the second cartridge channel. The first and second articulation links are axially movable to effect axial movement of the first and second cartridge channels in relation to each other to pivot the pivot member in relation to the shaft portion.

In certain embodiments, the surgical further includes a pivotal articulation member interconnecting the first articulation link to the second articulation link such that movement of the first articulation link in one direction effects movement of the second articulation link in an opposite direction.

BRIEF DESCRIPTION OF THE DRAWINGS

Various embodiments of the presently disclosed small diameter surgical stapler are described herein with reference to the drawings, wherein:

FIG. 1A is a side perspective view from the distal end of a stapler reload of the surgical stapler shown in FIG. 1;

FIG. 3A is a top, perspective view of a distal end of the upper housing half-section of the proximal body portion, a pivot member, and a connecting member with parts separated;

FIG. 9 is a side, perspective view of a cartridge channel of the stapler reload shown in FIG. 3;

FIG. 10 is a top view of the cartridge channel shown in FIG. 9;

FIG. 11 is an enlarged view of the indicated area shown in FIG. 10;

FIG. 12 is an enlarged view of the indicated area of detail shown in FIG. 9;

FIG. 13 is a perspective, partial cross-sectional view taken along section line 13-13 of FIG. 12.

FIG. 14 is a side, perspective view of a firing cam of the stapler reload shown in FIG. 3;

FIG. 15 is an enlarged view of the indicated area of detail shown in FIG. 14;

FIG. 16 is a perspective, partial cross-sectional view taken along section line 16-16 of FIG. 15;

FIG. 19 is a side, perspective view of the cartridge assembly of the stapler reload shown in FIG. 3 supported on the distal ends of the cartridge channels and firing cams;

FIG. 20 is an enlarged view of the indicated area of detail shown in FIG. 19;

FIG. 21 is a top view of the stapler reload shown in FIG. 1A with the tool assembly in an unapproximated position;

FIG. 22 is a cross-sectional view taken along section line 22-22 of FIG. 21;

FIG. 24 is an enlarged view of the indicated area of detail shown in FIG. 22;

FIG. 25 is a cross-sectional view taken along section line 25-25 of FIG. 21;

FIG. 29 is a side, cross-sectional view of the tool assembly of the stapler reload shown in FIG. 21 with the firing cams advanced into engagement with a second proximal-most staple;

FIG. 30 is an enlarged view of the indicated area of detail shown in FIG. 29;

FIG. 35 is a top perspective view of the proximal body portion of the stapler reload with the proximal tube removed and the upper housing half section removed;

FIG. 36 is a top perspective view of the upper housing half section of the proximal body portion of the stapler reload;

DETAILED DESCRIPTION OF EMBODIMENTS

Figure 1:
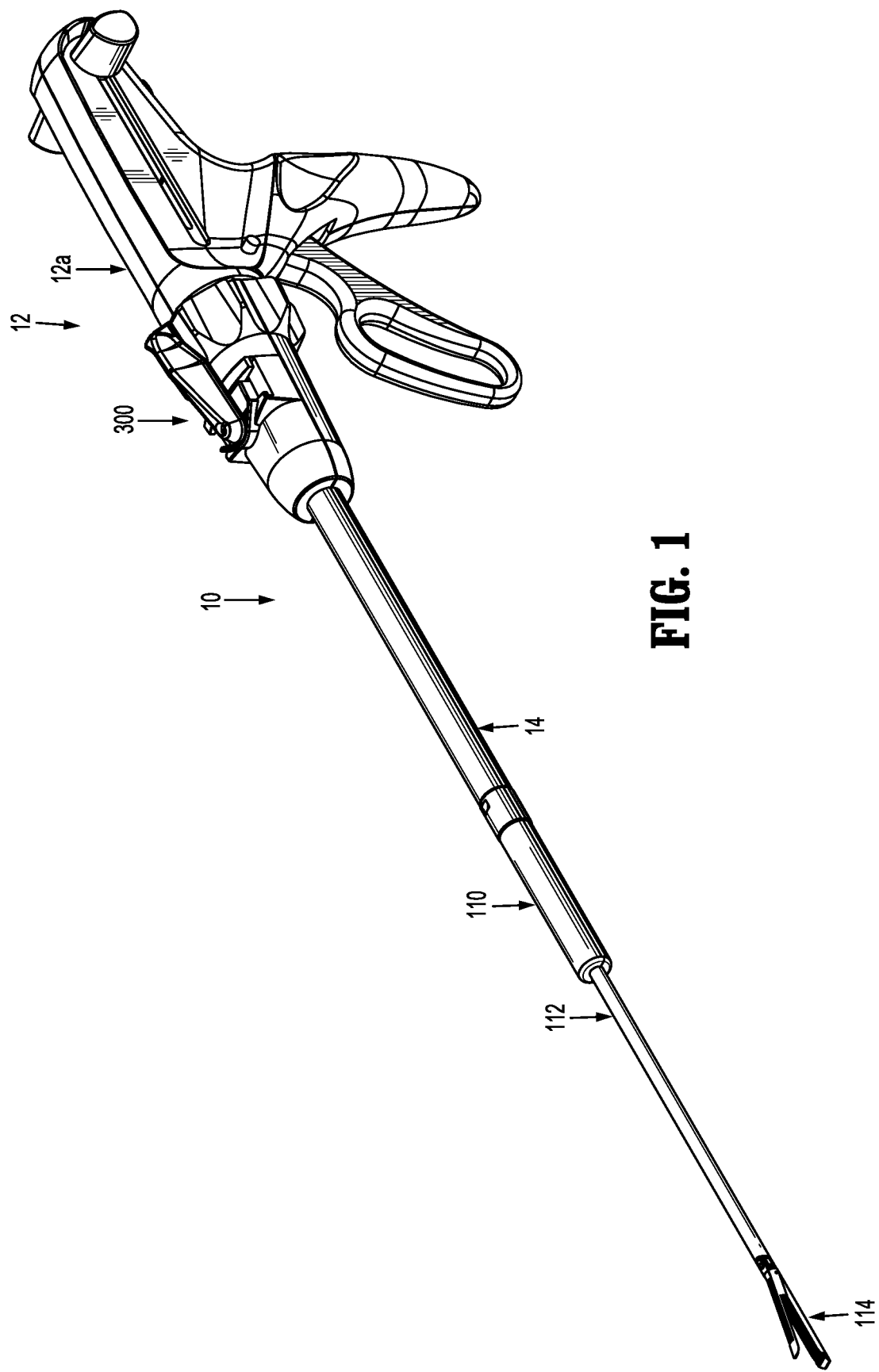
FIG. 1 is a side perspective view of an embodiment of the presently disclosed small diameter surgical stapler in an unapproximated position.

Embodiments of the presently disclosed small diameter surgical stapler will now be described in detail with reference to the drawings wherein like reference numerals designate identical or corresponding elements in each of the several views. In this description, the term "proximal" is used generally to refer to the portion of the apparatus that is closer to a clinician, while the term "distal" is used generally to refer to the portion of the apparatus that is farther from the clinician. In addition, the term "endoscopic" is used generally to refer to endoscopic, laparoscopic, arthroscopic, and any other surgical procedure performed through a small incision or a cannula inserted into a patient's body.

The presently disclosed surgical stapler includes a tool assembly which supports a series of staples which are supported and configured to be rotatably ejected from a staple cartridge into an anvil to suture tissue. The manner in which the staples are supported and ejected from within the staple cartridge facilitates the use of a small diameter tool assembly which includes staples capable of suturing thicker tissues than would normally be associated with tool assemblies with such a small diameter.

Figure 2:
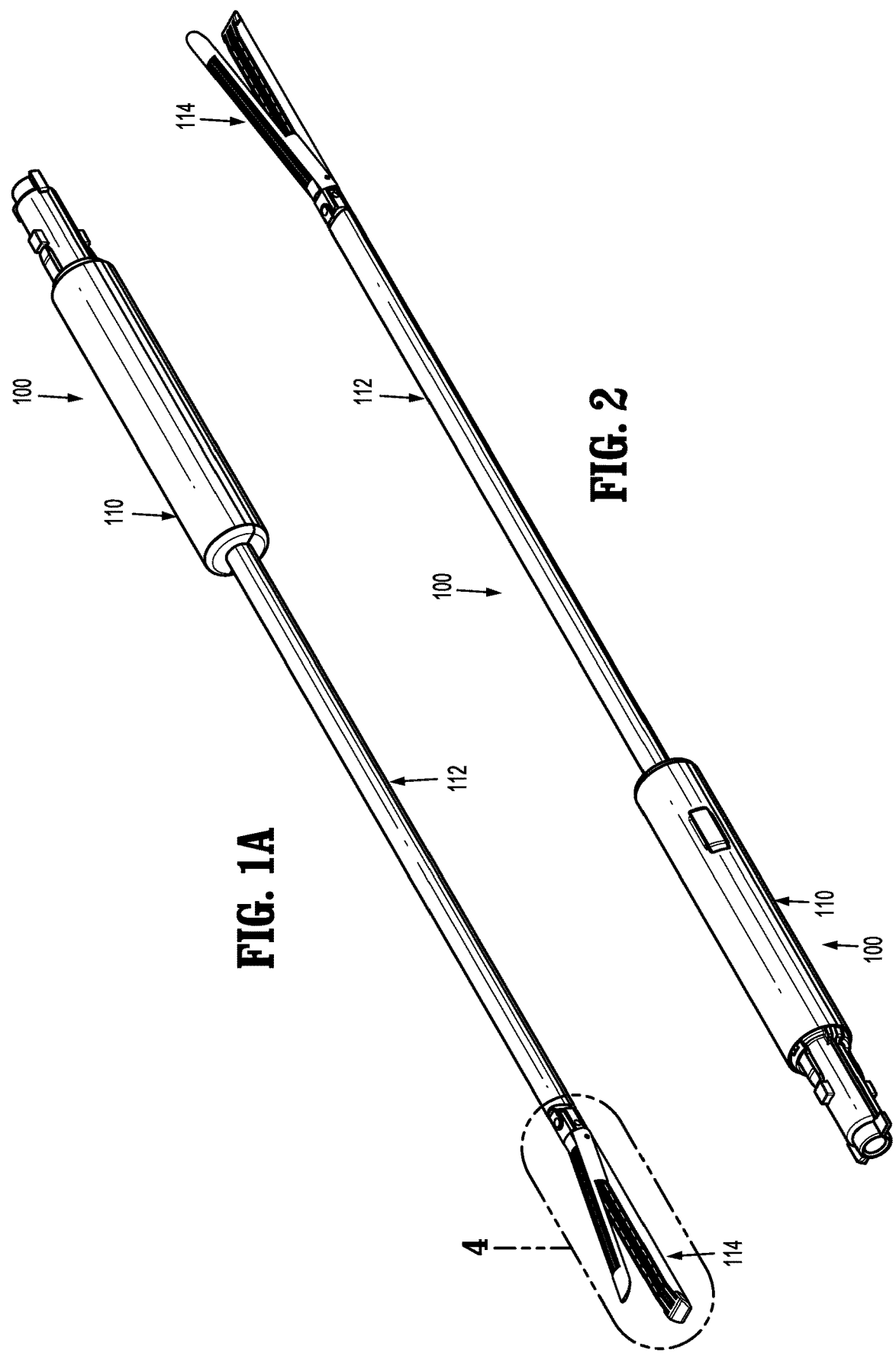
FIG. 2 is a side perspective view from the proximal end of the surgical stapler reload shown in FIG. 1A.

FIG. 1-2 illustrate the presently disclosed surgical stapler 10 which includes an actuating device 12 having a handle assembly 12a, a body portion 14 which extends distally from the handle portion 12, and a stapler reload 100 supported on a distal end of the body portion 14. The distal end of the body portion 14 is adapted to releasably engage a proximal end of the reload 100 such that actuation of the actuating device 12 effects operation of the reload 100. A suitable actuating device is disclosed in detail in U.S. Pat. No. 5,865,361 ("361 patent") and U.S. Pat. No. 7,143,924 ("924 patent") which are hereby incorporated herein in their entirety by reference. Although the presently disclosed actuating device is illustrated as a manually actuated handle assembly, it is envisioned that the reload 100 could be actuated by other known actuating devices including robotic devices, motorized devices, and/or electrically or mechanically driven devices.

In an alternate embodiment, the reload 100 can be fixedly attached to the distal end of the handle assembly 12 and only a cartridge assembly of a tool assembly can be removable and replaceable. Alternatively, a removable and replaceable reload can also have a removable and replaceable cartridge.

Figure 3:
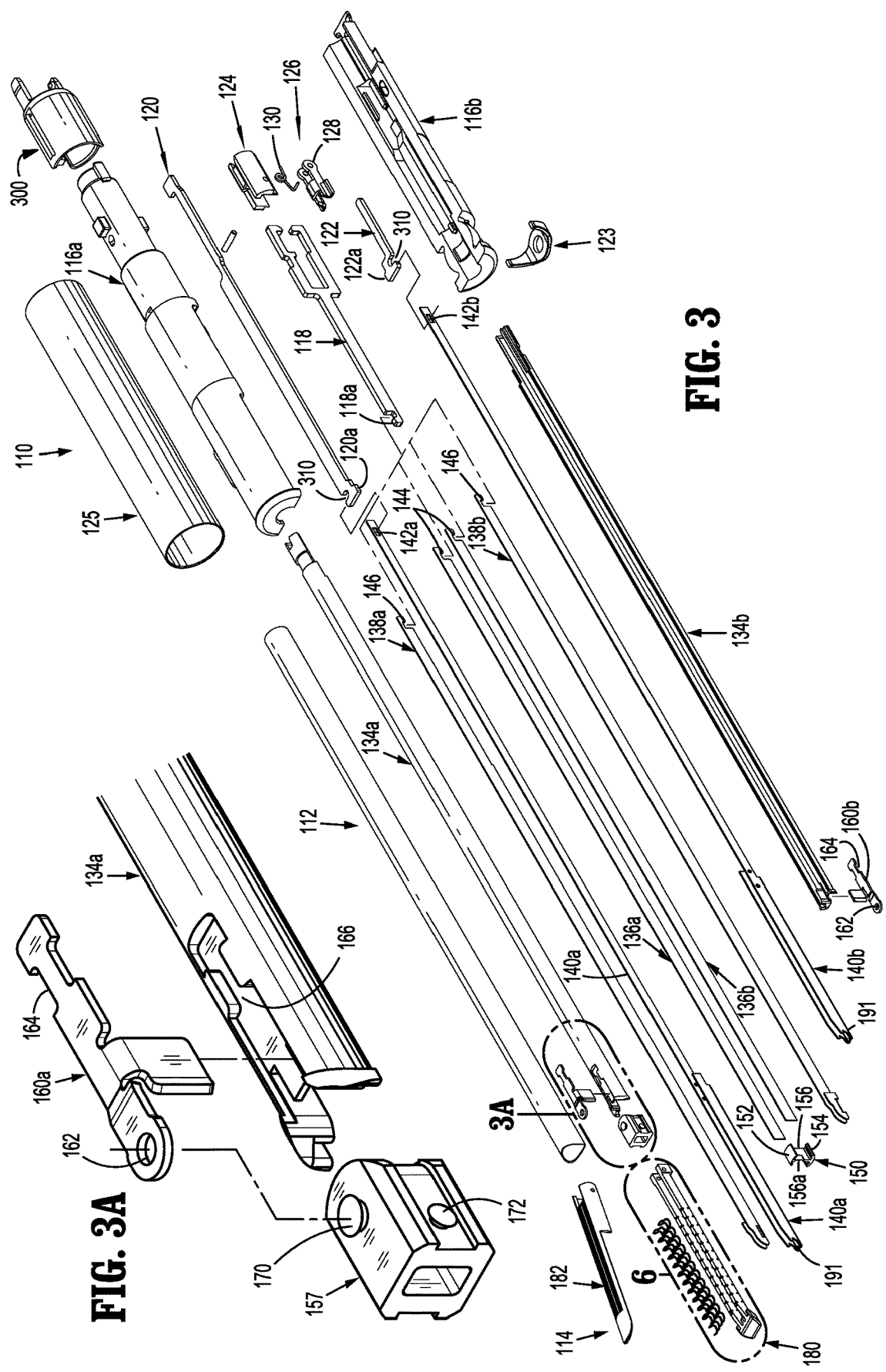
FIG. 3 is a side perspective, exploded view of the stapler reload shown in FIG. 1A.
Figure 4:
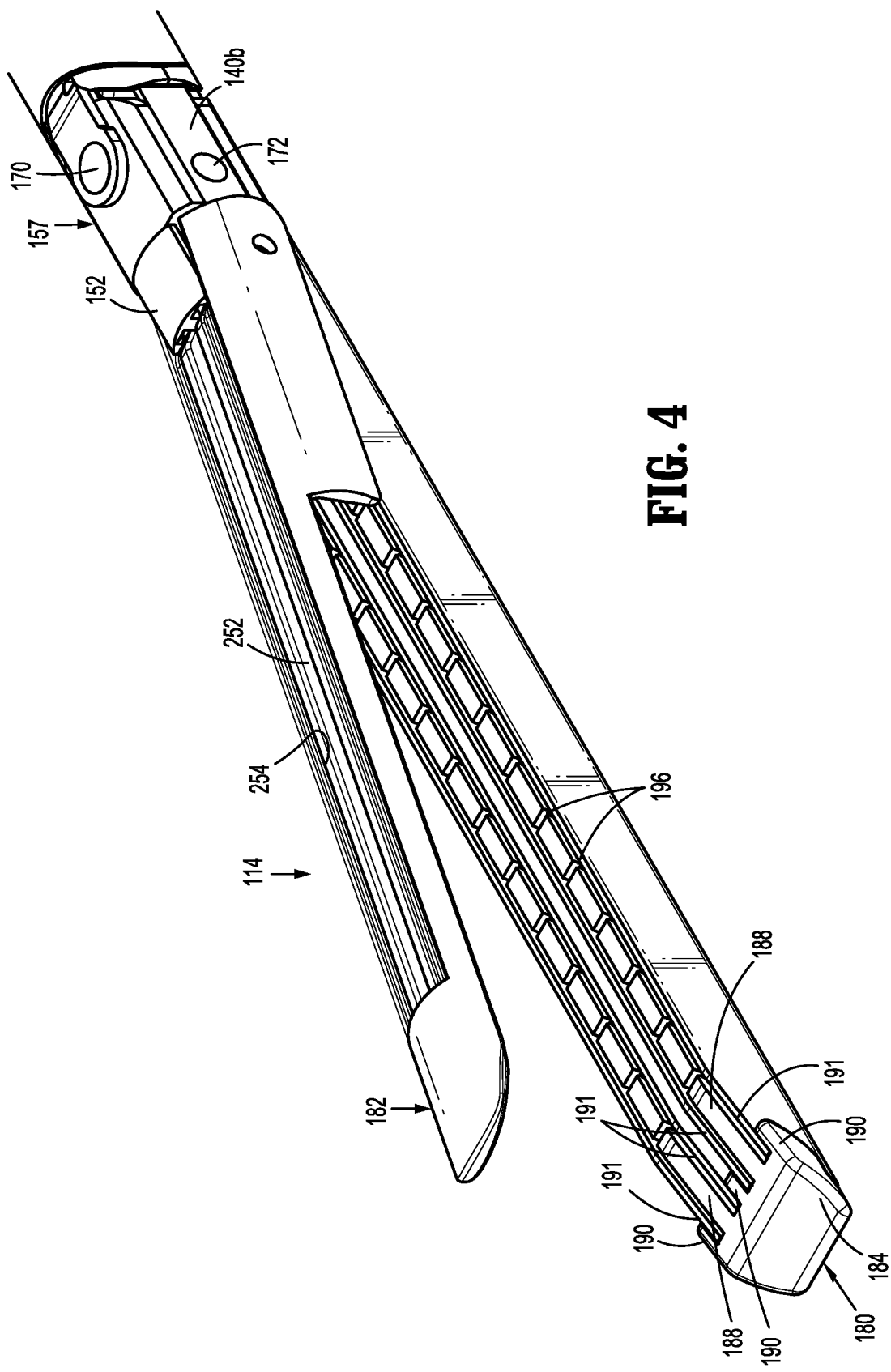
FIG. 4 is an enlarged view of the indicated area of detail shown in FIG. 1A.
Figure 5:
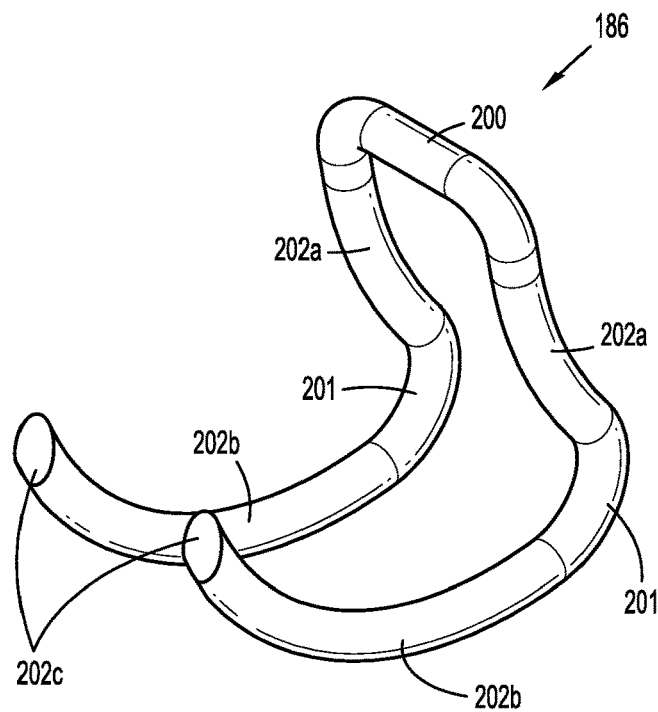
FIG. 5 is a side perspective view of a staple of the stapler reload shown in FIG. 3.
Figure 6:
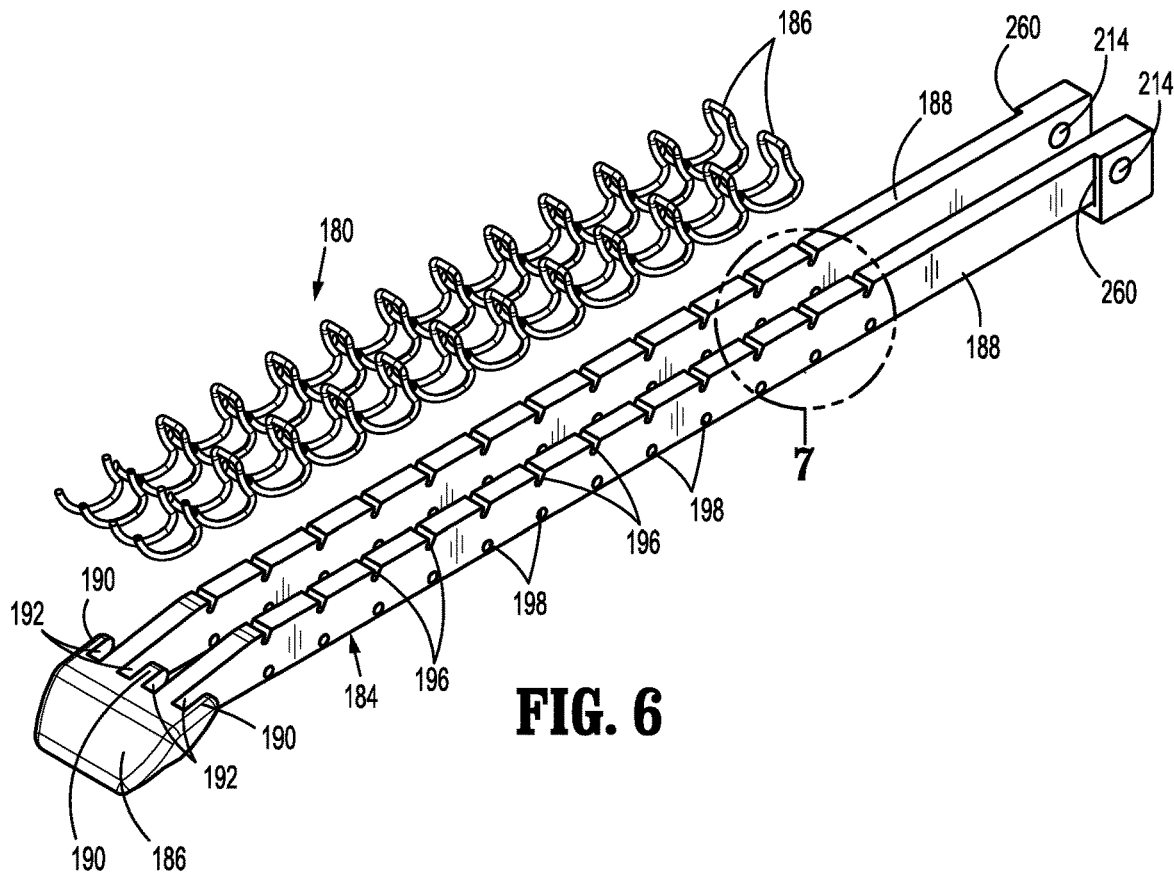
FIG. 6 is a side perspective, exploded view of the cartridge and staples of the stapler reload shown in FIG. 3.
Figure 7:
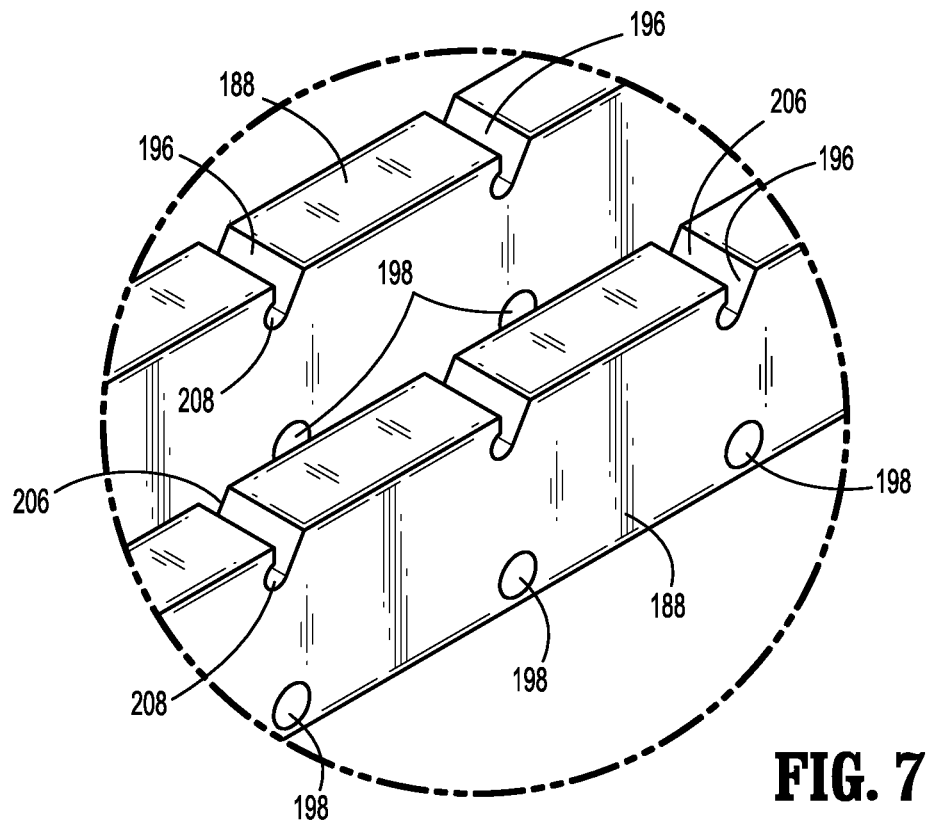
FIG. 7 is an enlarged view of the indicated area of detail shown in FIG. 6.
Figure 8:
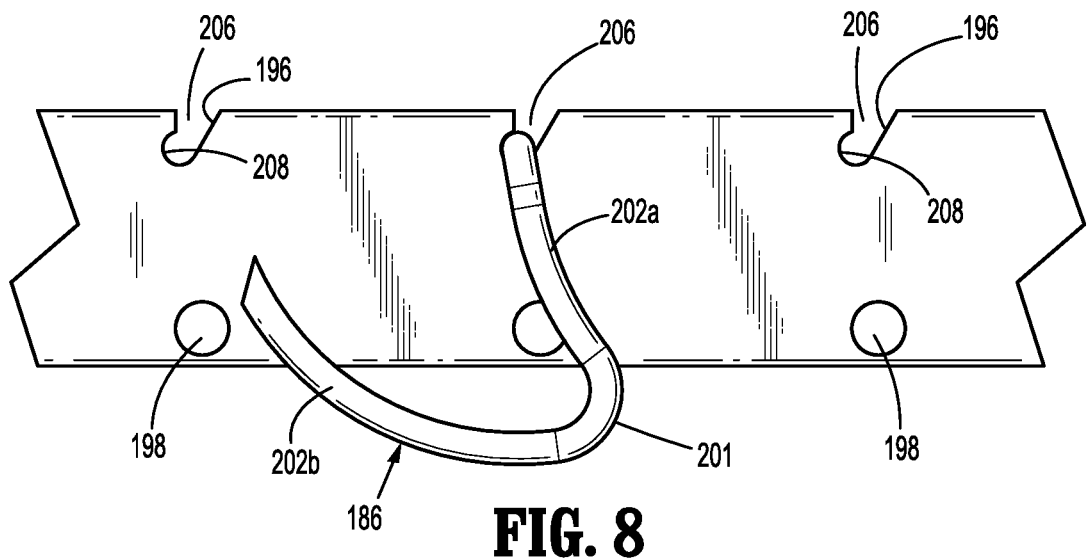
FIG. 8 is a side, cutaway view of the cartridge body supporting a staple.
Figures 17, 18:
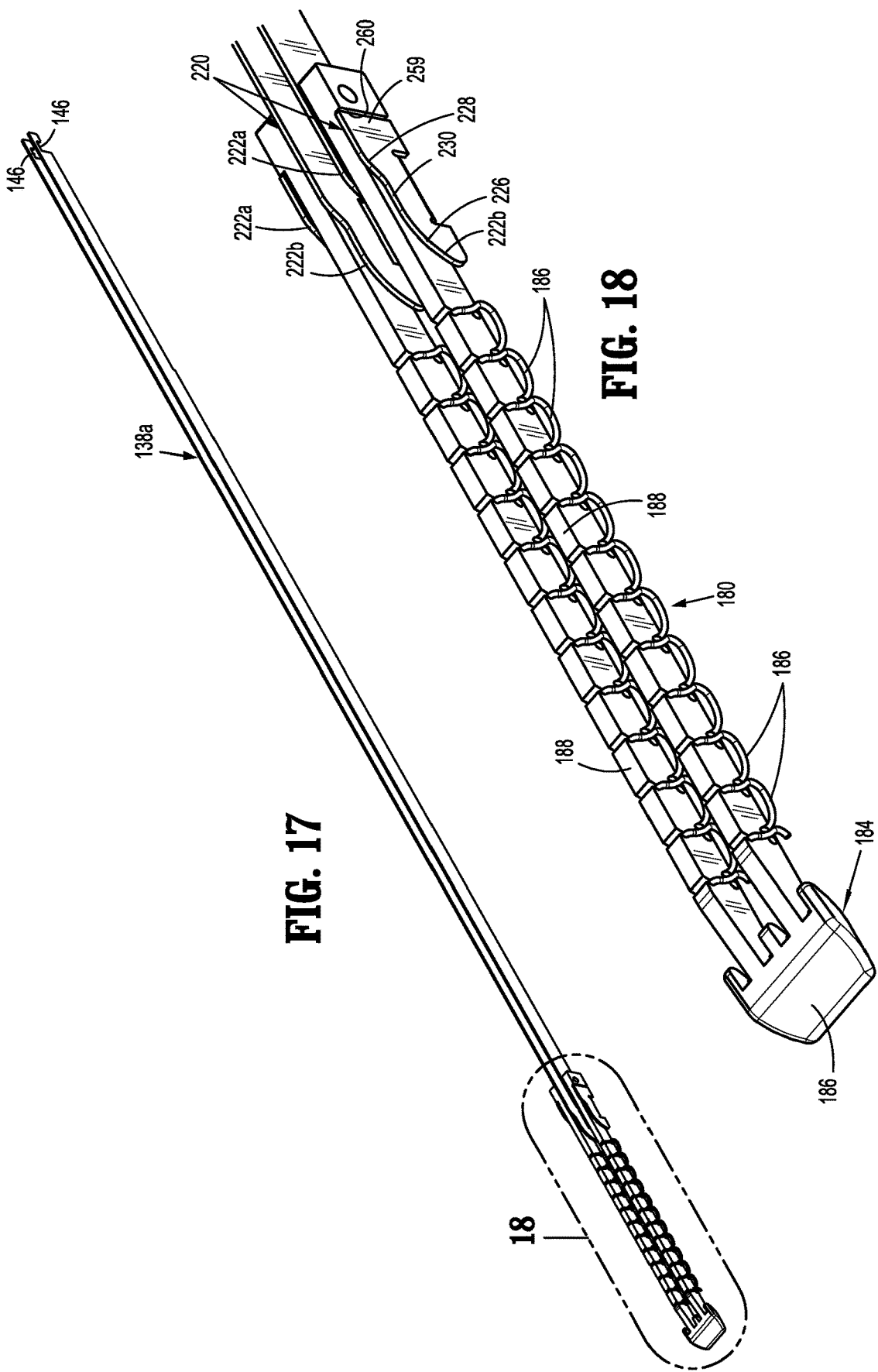
FIG. 17 is a side, perspective view of the cartridge assembly of the stapler reload shown in FIG. 3 supported on a distal end of the firing cams.
FIG. 18 is an enlarged view of the indicated area of detail shown in FIG. 17.
Figure 23:
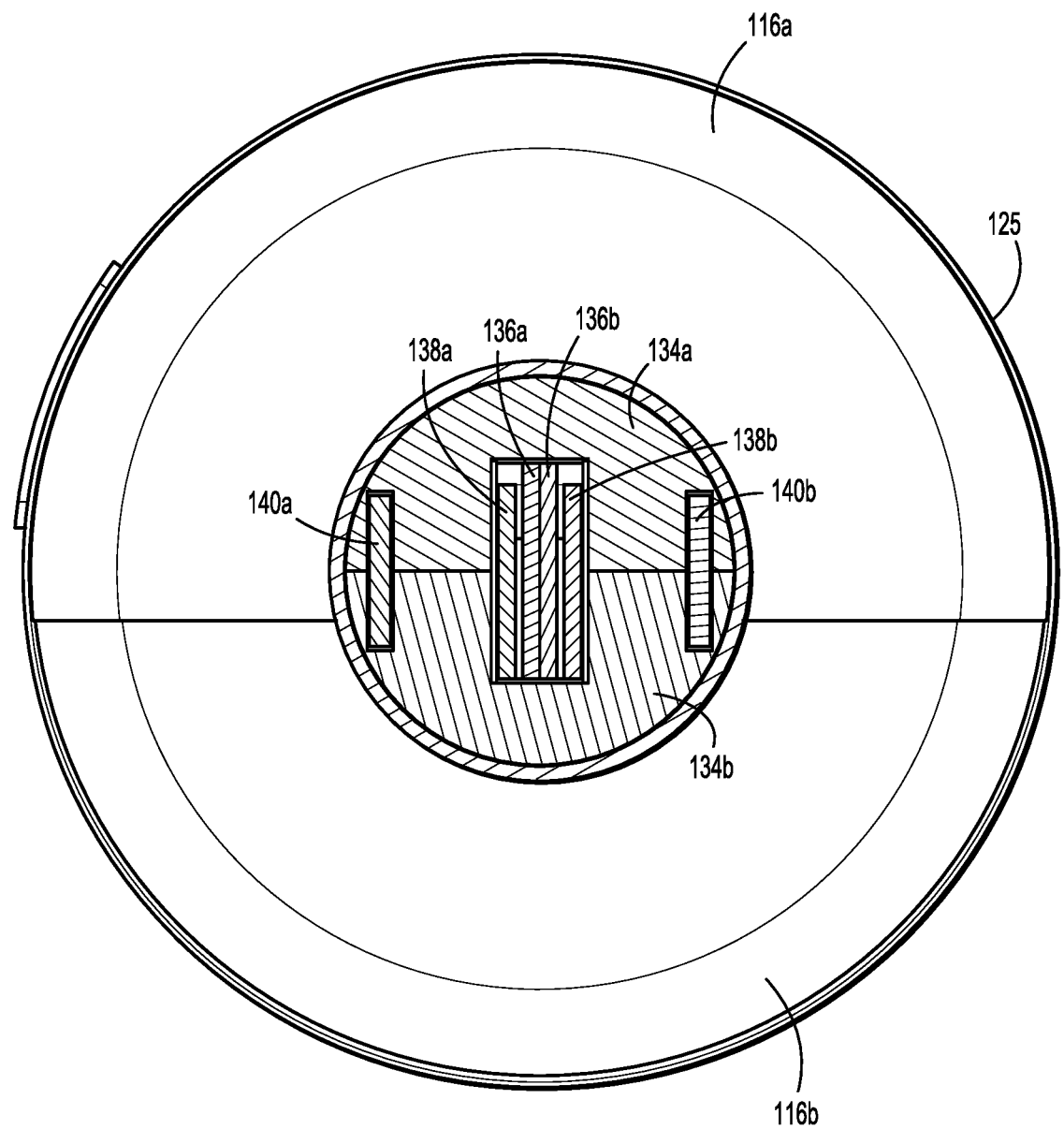
FIG. 23 is a cross-sectional view taken along section line 23-23 of FIG. 21.

Referring also to FIG. 3, the reload 100 includes a proximal body portion 110, an elongated shaft portion 112 and a tool assembly 114. The proximal body portion 110 includes an inner housing 116 defined by an upper housing half-section 116a and a lower housing half-section 116b. The housing half-sections 116a and 116b define channels which slidably receive a proximal drive member 118, a first articulation link 120 and a second articulation link 122. The housing half-sections 116a and 116b are received within a proximal tube 125.

The first articulation link 120 is connected to the second articulation link 122 by an articulation member 123 which will be described in detail below. The proximal drive member 118 supports a drive coupler 124 which is adapted to engage a control rod (not shown) of the actuating device 12 (FIG. 1) to operate the tool assembly 114 of the reload 100. The proximal drive member 118 also supports a locking assembly 126 which includes a locking device 128 and a spring 130. Operation of the drive coupler 124 and the locking assembly 126 are described in the '361 patent which is incorporated herein by reference. A distal end of the proximal drive member 118 includes a hook portion 118a. Similarly, distal ends of the first articulation link 120 and the second articulation link 122 include hook portions 120a and 122a, respectively. Each of these hook portions will be described in further detail below.

The elongated shaft portion 112 includes an inner housing 134 defined by upper and lower housing half-sections 134a and 134b. A proximal end of the inner housing 134 is received within the distal end of the inner housing 116 of the proximal body portion 110 and includes an annular recess 135 (FIG. 25). The annular recess 135 receives a protrusion 116c formed within the inner housing 116 to axially secure the inner housing 116 of the proximal body portion 110 to the inner housing 134 of the shaft portion 112. The upper and lower housing half-sections 134a and 134b define channels which slidably receive a pair of distal drive members 136a and 136b, a pair of firing cams 138a and 138b, and a pair of cartridge channels 140a and 140b. A proximal end of each of the cartridge channels 140a and 140b defines a cutout 142a and 142b, respectively. The cutouts 142a and 142b of the cartridge channels 140a and 140b receive the hook portions 120a and 122a, respectively of the first and second articulation links 120 and 122 such that linear movement of the first and second articulation links 120 and 122 effects linear movement of the cartridge channels 140a and 140b as will be discussed in further detail below. A proximal end of each of the distal drive members 136a and 136b includes a hook portion 144 which is engaged with the hook portion 118a of the proximal drive member 118. Similarly, a proximal end of each of the firing cams 138a and 138b includes a hook portion 146 which is also engaged with the hook portion 118a of the proximal drive member 118. Movement of the proximal drive member 118 effects corresponding movement of the distal drive members 136a and 136b and of the firing cams 138a and 138b as will be discussed in further detail below.

The distal end of the distal drive members 136a and 136b are secured to a working member 150 such as by welding. In one embodiment, the working member 150 includes an upper beam 152, a lower beam 154 and a vertical strut 156 interconnecting the upper and lower beams 152 and 154. A cutting edge 156a is formed in or supported on a distal end of the vertical strut 156. The vertical strut 156 is movably positioned between the cartridge channels 140a and 140b, the firing cams 138a and 138b and the legs 188 of the cartridge body 184. The working member 150 is positioned and configured to move through the tool assembly 114 when the distal drive members 136a and 136b are advanced distally within the elongated shaft portion 112 as will be discussed in detail below.

Referring also to FIG. 3A, a pivot member 157 is secured to a distal end of the shaft housing half-sections 134a and 134b by upper and lower connecting members 160a and 160b. Each connecting member 160a and 160b includes a distal end which defines an opening 162 and a proximal end 164 which defines a stepped configuration. The stepped configuration of the proximal end 164 is received within a cutout 166 formed in the distal end of each of the upper and lower shaft housing half-sections 134a and 134b to axially fix the upper and lower connecting members 160a and 160b to the upper and lower shaft housing half-sections 134a and 134b, respectively. The openings 162 of the connecting members 160a and 160b each receive a respective pivot pin 170 (only one shown) formed on the upper and lower surfaces of the pivot member 156 to pivotally secure the pivot member 157 to the shaft housing half-sections 134a and 134b. The pivot member 157 also includes two transversely extending posts 172. Each post 172 is received in an opening 210a (FIG. 13) formed in one of the cartridge channels 140a and 140b to secure the pivot member 156 between the cartridge channels 140a and 140b.

Referring to FIGS. 3-8, the tool assembly 114 includes a cartridge assembly 180 and an anvil 182. The cartridge assembly 180 (FIG. 6) includes a cartridge body 184 and a plurality of staples that initially have the shape of an open loop. In certain embodiments, the staples are generally U-shaped staples 186 with two prongs or legs. The cartridge body 184 includes a tapered distal end 186 and first and second spaced legs 188. The tapered distal end 186 of the cartridge body 184 functions as a tissue guide and includes three proximally extending fingers 190. One of the fingers 190 is positioned on each side of each of the spaced legs 188 with one finger 190 being positioned between the spaced legs 188. Each of the fingers 190 defines a recess 192 with an adjacent leg 188. The recesses 192 receive the distal ends 191 of the firing cams 138a and 138b to secure the cartridge body 184 to the distal end of the firing cams 138a and 138b.

Each of the first and second spaced legs 188 includes a series of spaced notches 196 and a pair of dimples 198 associated with each notch 196. Each of the dual staples 186 includes a backspan 200 and a pair of spaced U-shaped curved legs or prongs 201. Each of the curved legs 201 includes a proximal leg portion 202a and a distal leg portion 202b. One end of the proximal leg portion 202a is connected to the backspan 202 and the other end of the proximal leg portion 202a is connected to one end of the distal leg portion 202b. The other end of the distal leg portion 202b includes a tapered tip 202c. The distal leg portion 202b is curved upwardly and rearwardly towards the backspan 202.

Each notch 196 of the spaced legs 188 has a wide mouth 206 which converges to a cylindrical slot 204 (FIG. 8) which is configured to receive the backspan 202 of a staple 186 in a snap-fit manner. With the backspan 202 of a staple 186 positioned in the cylindrical slot 204 of a notch 196, the proximal leg portions 202a of each curved leg of the staple 186 engages one of the dimples 198 associated with each notch 196 to stabilize the staple 186 on a respective leg 188 of the cartridge body 184. In this position, the backspan 202 extends transversely across the cartridge body 184 and a curved leg of each staple 186 is positioned on each side of the leg 188 of the cartridge body on which the staple 186 is supported. The distal leg portions 202b of each the staples 186 engage the proximal leg 202a of a distally positioned adjacent staple 186 to further stabilize the staple 186 on the cartridge body 184 and provide a guide surface for the staple 186 as the staple 186 is being fired as will be discussed in further detail below.

Referring to FIGS. 9-13, each of the cartridge channels 140a and 140b (FIG. 3) includes a resilient body that extends from the proximal body portion 110 to the tool assembly 114. A distal end of each cartridge channel 140a and 140b includes a U-shaped member 208 which receives a leg 188 of the cartridge body 184. Each of the U-shaped members 208 including a proximal opening 210a and a distal opening 210b. The proximal opening 210a receives the post 172 (FIG. 3) of the pivot member 157 to secure the cartridge assembly 180 to the pivot member 157. The distal opening 210b receives a pin (not shown) which extends through the opening 210b and an opening 214 (FIG. 6) in the proximal end of each of legs 188 to secure the proximal end of the legs 188 of cartridge body 184 to the respective cartridge channels 140a and 140b. The distal end 191 of each U-shaped member 208 is received in adjacent recesses 192 formed on opposite sides of each leg 188 of cartridge body 184 and is defined by a pair of cutouts 191a and distally extending fingers 191b (FIG. 12). A bottom wall 193 (FIG. 13) of each cartridge channel 140a and 140b is w-shaped to provide channels to facilitate rotation of the staples 186 within the cartridge channels 140a and 140b.

Referring to FIGS. 14-16, the distal end 220 of each firing cam 138a and 138b defines a cam member 222. The cam member 222 has a wavy, curved shape. In certain embodiments, the cam member includes a portion for moving the staple into engagement with an anvil pocket and at least one portion for forming the staple into a closed configuration. In the embodiment shown, the cam member has a portion for partially forming the staple, and a portion for deforming the staple into its final configuration.

The cam member 222 has first and second cam surfaces 222a and 222b. Each cam member 222 is U-shaped and defines a channel 224 which receives a respective one of legs 188 (FIG. 6) of the cartridge body 184 such that each cam member 222 is slidable along the leg 188 of the cartridge body 184 into engagement with staples 186. Each of the cam surfaces 222a and 222b is curved and defines a first curved surface 226 and a second curved surface 228 which are interconnected by a plateau 230. The cam surfaces 222a and 222b increase in height from a distal end of each of the cam surface 222a and 222b towards a proximal end of the cam surfaces 222a and 222b. The first curved surface 226 is configured to initiate deformation of a leg 201 of a staple 186 and the second curved surface 228 is configured to complete deformation of the leg 201 of a staple and to disengage the leg from the cylindrical opening of a notch 196 of the cartridge body 184.

Figure 33:
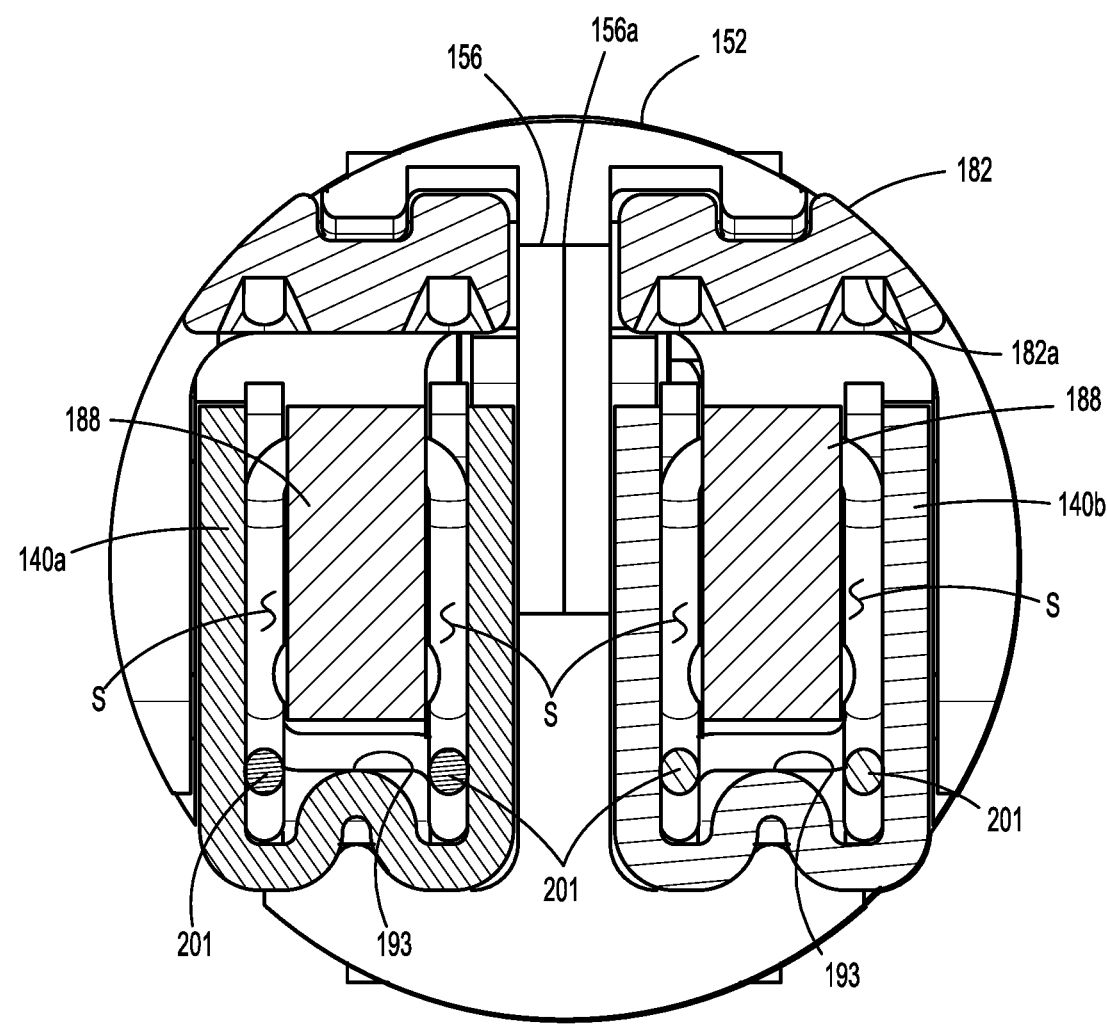
FIG. 33 is a cross-sectional view taken along section line 33-33 of FIG. 31.
Figure 34:
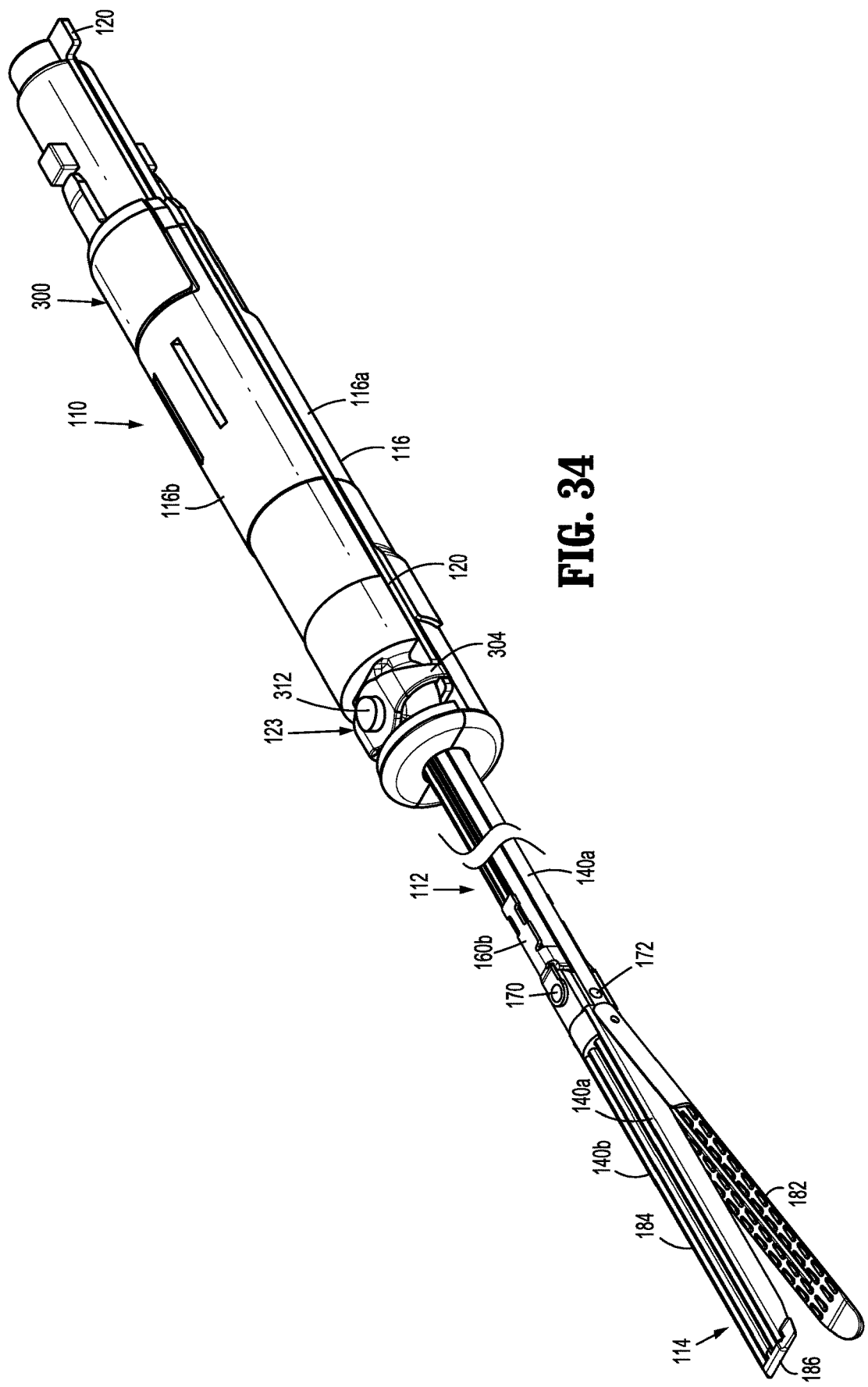
FIG. 34 is a side, perspective view of the stapler reload shown in FIG. 1A in a non-articulated and unapproximated position with the proximal tube of the proximal body portion and the shaft tube of the shaft portion removed.
Figure 37:
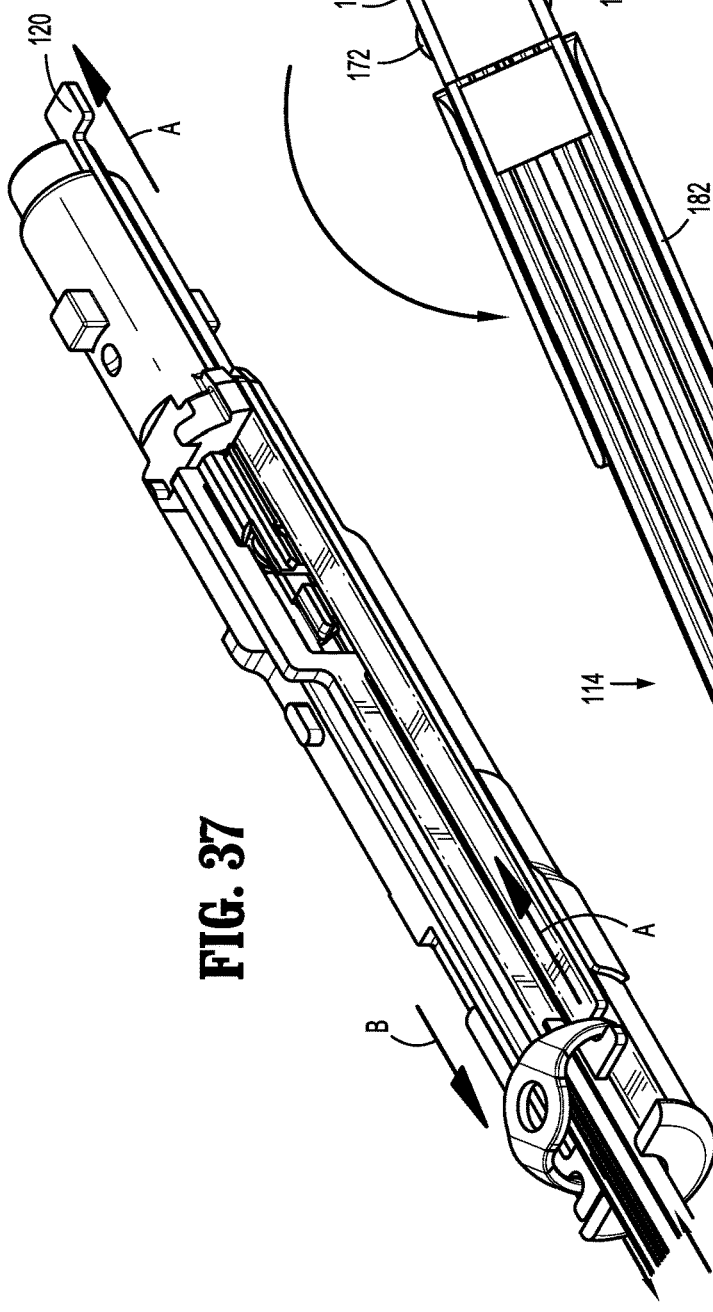
FIG. 37 is a top, perspective view of the proximal body portion of the stapler reload shown in FIG. 35 with the proximal tube and the upper housing half section removed and the articulation member rotated.
Figure 38:
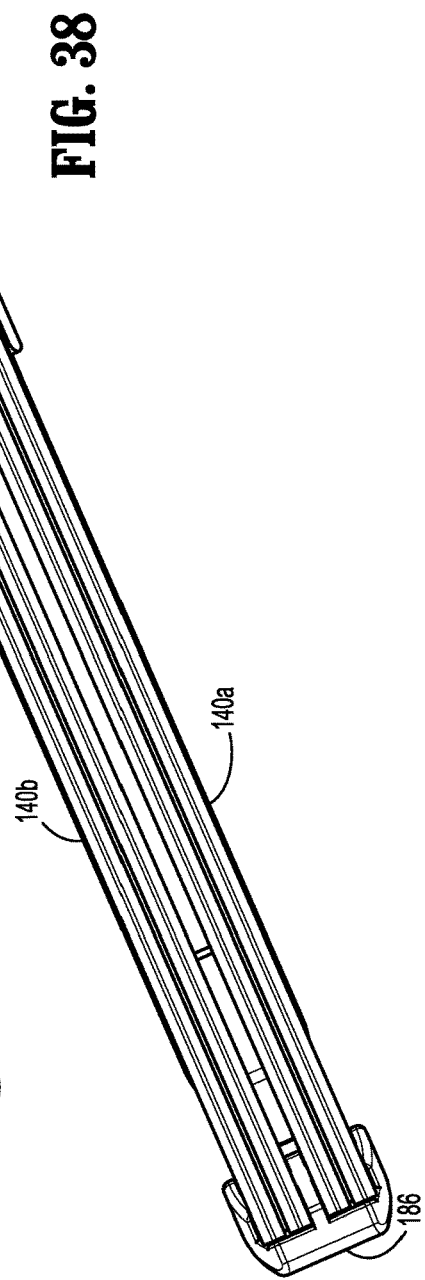
FIG. 38 is a top view of the tool assembly of the stapler reload shown in FIG. 26 in an articulated position.

Referring also to FIGS. 17-20, when the cartridge channels 140a and 140b are positioned about the legs 188 of the cartridge body 184 and secured to the cartridge body 184, a space "s" (FIG. 33) is defined between sidewalls of the legs 188 and inner walls of the cartridge channels 140a and 140b. A cam surface 222a, 222b formed on the distal end 220 of each of the firing cams 138a and 138b is slidably supported in the space "s" defined between the legs 188 and the cartridge channels 140a and 140b. When the firing cams 138a and 138b are advanced distally from a retracted position to an advanced position, the cam surfaces 222a and 222b are moved between the legs 188 and the cartridge channels 140a and 140b into sequential contact with the staples 186 to urge the staples 186 from the cartridge body 184 into the staple forming depressions 182a (FIG. 22) of the anvil 182 as will be discussed in further detail below.

Referring to FIGS. 3 and 21-25, the anvil 182 defines an elongated slot 252 and on elongated cavity 254. The vertical strut 156 passes through the elongated slot 252 such that the upper beam 152 is slidably positioned in the elongated cavity 254 of the anvil 182. A proximal end of the anvil 182 defines a tapered cam surface 256 which is positioned in engagement with a distal end of the upper beam 152 of the working member 150 when the anvil 182 is pivoted to an open position as shown in FIG. 22. The lower beam 154 is positioned to move along the bottom surface of the cartridge channels 140a and 140b.

Referring briefly again to FIG. 3, the reload 100 includes a locking member 300 which is rotatably supported about a proximal end of the proximal body portion 110. The locking member 300 is movable from a first position (FIG. 25) in which the locking member 300 blocks distal advancement of the proximal drive member 118 to a second position in which the locking member does not block movement of the proximal drive member 118. U.S. Pat. No. 7,143,924 describes the locking member 300 and its method of operation in detail and is incorporated herein by reference in its entirety.

Referring again to FIGS. 21-25, when the proximal drive member 118 (FIG. 25) is in a retracted position, the distal drive members 136a and 136b and the firing cam 138a and 138b are also in a retracted position. In the retracted position of the distal drive members 136a and 136b, the distal end of the upper beam 152 of the working member 150 is positioned in engagement with the tapered cam surface 256 of the anvil 182 to urge the anvil 182 to an open position spaced from the cartridge body 184 (FIG. 22). In the retracted position of the firing cams 138a and 138b, the cam surfaces 222a and 222b of each of the firing cams 138a and 138b is positioned proximally of the staples 186 (FIG. 24) such that a proximal end 259 (FIG. 18) of cam surface 222b of each firing cam 138a and 138b is in abutment with a shoulder 260 (FIG. 6) of a respective leg 188 of the cartridge body 184.

Figure 26:
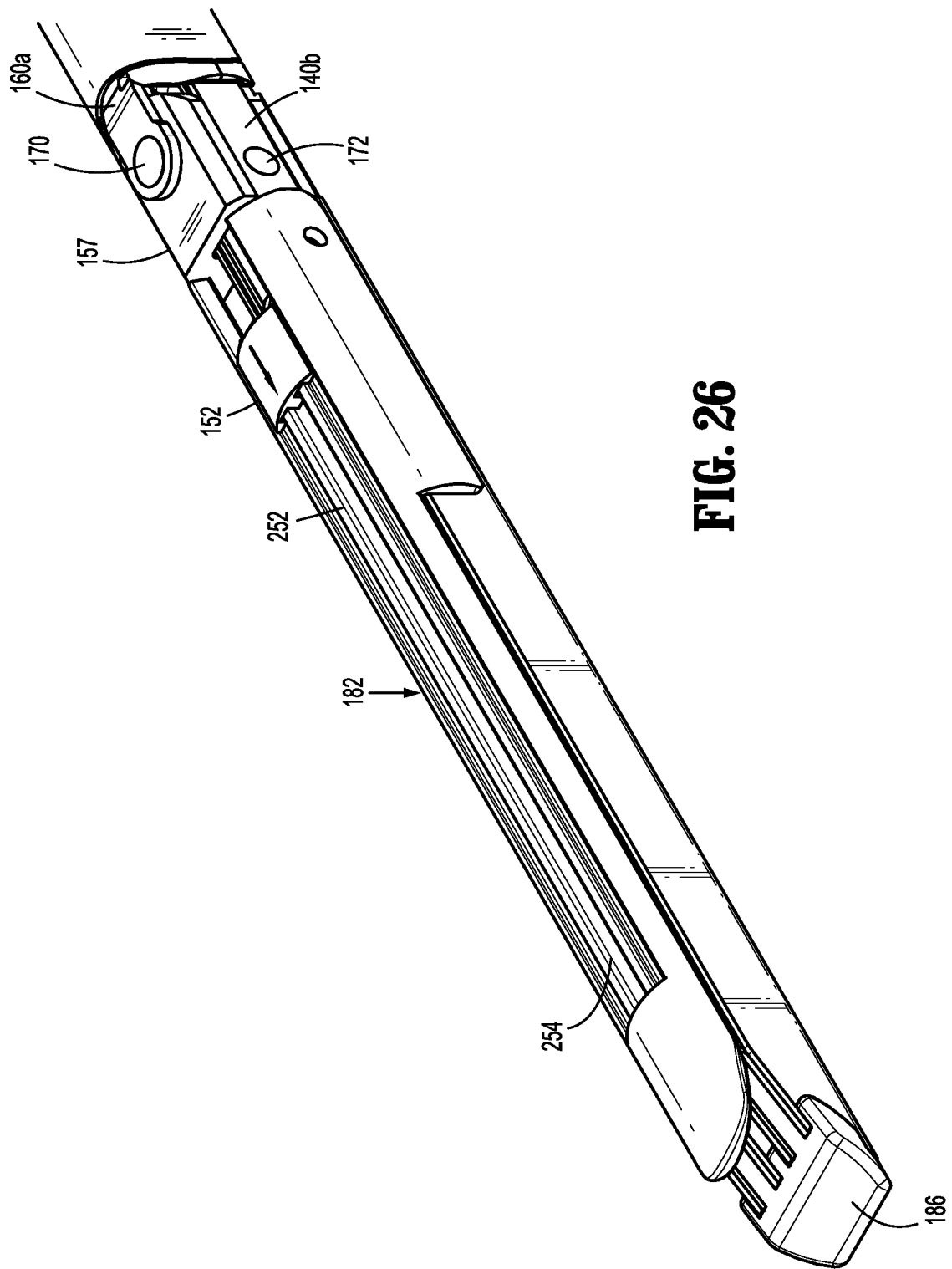
FIG. 26 is a top, perspective view of the tool assembly of the stapler reload shown in FIG. 21 with the tool assembly in the approximated position and the firing cams advanced into engagement with a proximal-most staple of the plurality of staples.
Figure 27:
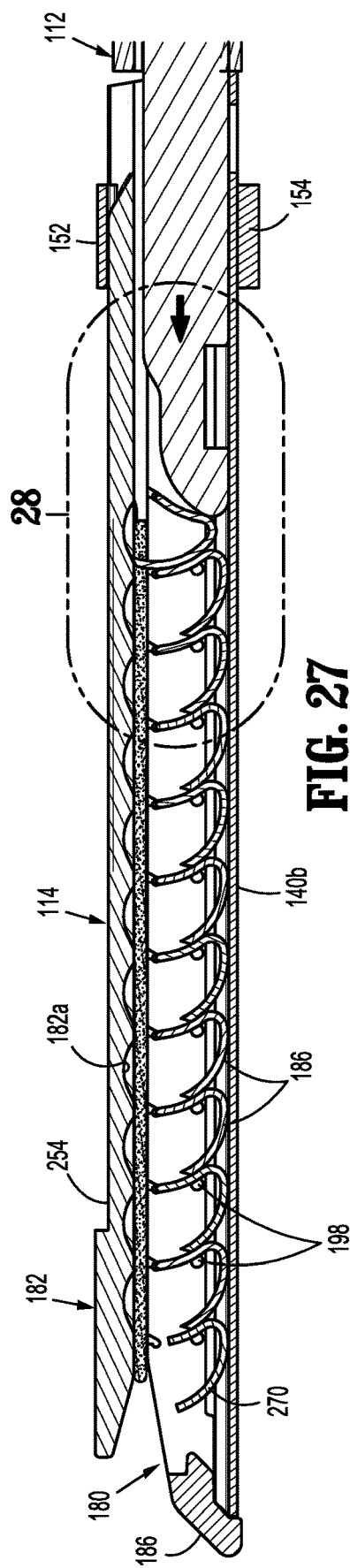
FIG. 27 is a side, cross-sectional view of the tool assembly of the stapler reload shown in FIG. 26.
Figure 28:
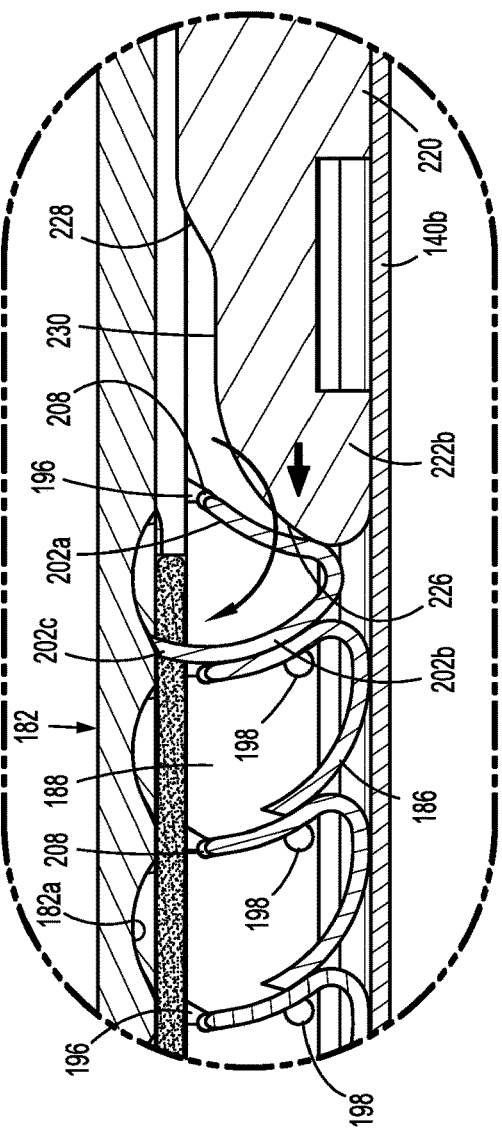
FIG. 28 is an enlarged view of the indicated area of detail shown in FIG. 27.
Figure 31:
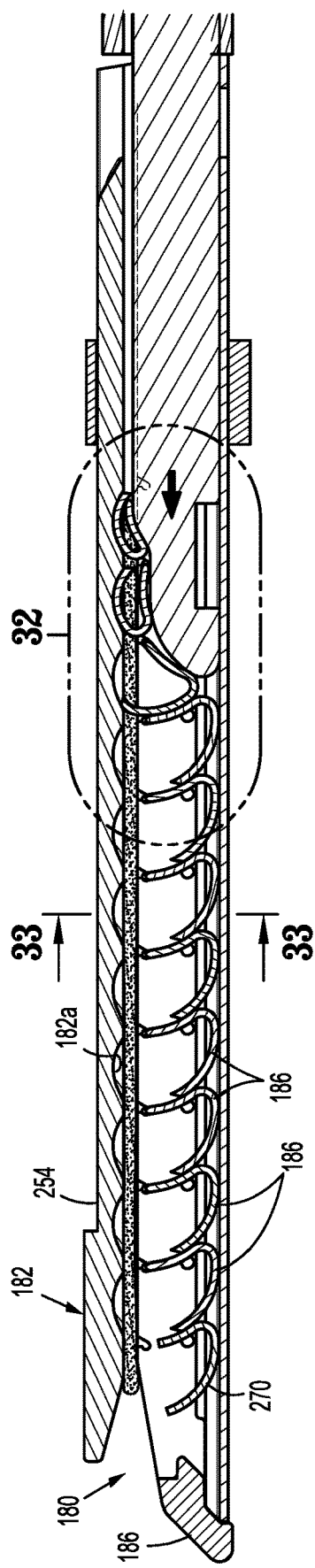
FIG. 31 is a side, cross-sectional view of the tool assembly of the stapler reload shown in FIG. 21 with the firing cams advanced to disengage the proximal-most staple of the plurality of staples from a notch in the cartridge body.

Referring to FIGS. 26-28, when the proximal drive member 118 is advanced by operation of the actuating device 12 (FIG. 1), the upper beam 152 of the working member 150 is moved over the tapered cam surface 256 (FIG. 27) of the anvil 182 to pivot the anvil 182 to an approximated position (FIG. 26).

Figure 32:
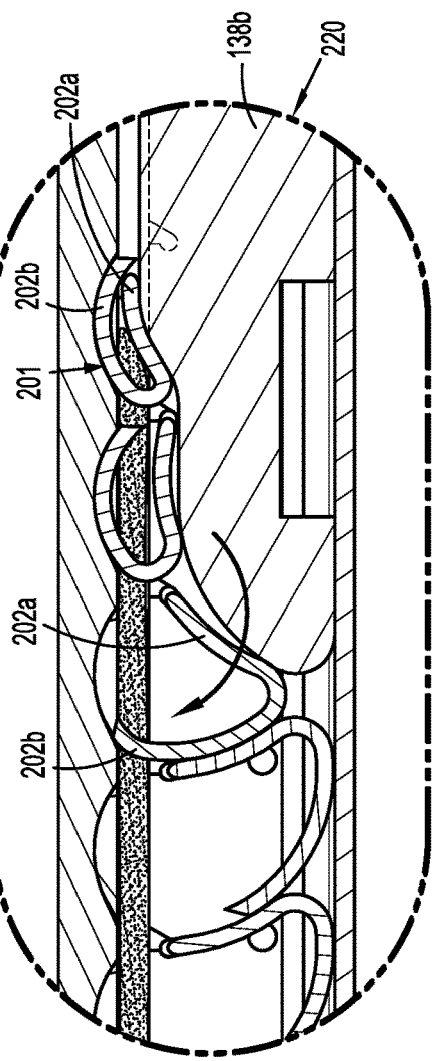
FIG. 32 is an enlarged view of the indicated area of detail shown in FIG. 31.

Referring also to FIGS. 29-33, continued advancement of the proximal drive member 118 (FIG. 25), moves cam surfaces 222a and 222b (only 222b is shown in FIGS. 29-33) of each of the firing cams 138a and 138b sequentially into contact with the staples 186. More particularly, when the firing cams 138a and 138b are advanced about legs 188 of cartridge body 184, the cam surfaces 222a and 222b sequentially engage the proximal leg portions 202a of the staples 186 to rotate or pivot the staples 186 about the backspan 202 within the cylindrical slot 208 of a respective notch 196. As the proximal leg portion 202a of each staple 186 moves along the first curved cam surface 226 of cam surfaces 222a and 222b, each staple 186 is pivoted or rotated upwardly such that the proximal leg portion 202a moves over a respective dimple 198 and the tapered tip 202c moves into a staple forming depression 182a of the anvil 182 to initiate deformation of the staple 186. When the proximal leg portion 202a of each staple 186 moves over the plateau 230 and along the second curved surface 228, the second curved surface 228 of the cam surface 222a and 222b fully deforms and disengages each staple 186 from the cylindrical slot 208 of a respective notch 196. As shown in FIGS. 30 and 32, the proximal leg portion 202a of each staple 186 serves as a guide for an adjacent proximal staple 186 as the adjacent proximal staples 186 are cammed from the cartridge body 184. The distal-most staple 270 in each row of staples 186 is a dummy staple and is not fired from the cartridge body 184. The dummy staple 270 provides a guide surface for the adjacent proximal staple 186. Alternately, the dummy staple 270 may be replaced with guide grooves or dimples formed on the cartridge body 184.

Referring to FIGS. 34-38, the tool assembly 114 can be articulated by movement of the cartridge channels 140a and 140b in opposite directions in relation to each other. As discussed above, the cartridge channels 140a (FIG. 3) and 140b extend from the proximal body portion 110 through the elongated shaft portion 112 to the tool assembly 114. A distal end of each of the cartridge channels 140a and 140b is connected to the pivot member 157 by a respective post 172 (FIG. 3A) which extends through the proximal openings 210a of the cartridge channel 140a and 140b. The proximal ends of the cartridge channels 140a and 140b include cutouts 142a and 142b, respectively, which receive hook portions 120a and 122a of the articulation rods 120 and 122, respectively, to connect the articulation rods 120 and 122 to the cartridge channels 140a and 140b. The first and second articulation links 120 and 122 are slidably supported between the housing halves 116a and 116b of the proximal body portion 110. The first articulation link 120 has a distal end connected to the cartridge channel 140a and a proximal end connected to an articulation assembly 300 (FIG. 1) of the actuating device 12 (FIG. 1). The articulation member 123 includes a C-shaped body 302 having spaced fingers 304 and 306 and a central opening 308 (FIG. 35). The fingers 304 and 306 are received in cutouts 310 formed in the distal end of first and second articulation links 120 and 122. The central opening 308 receives a housing post 312 (FIG. 36) formed on housing half 116b of the central body portion 110 such that movement of the first articulation link 120 in one direction as indicated by arrow "A" in FIG. 37 causes the articulation member 123 to pivot about the housing post 312 to cause movement of the second articulation link 122 in a second direction as indicated by arrow "B" in FIG. 37.

In use, when the first articulation link 120 is moved by the articulation assembly 300 in direction A, the cartridge channel 140a, which is axially fixed to the first articulation link 120 by placement of hook portion 120a in cutout 142a (FIG. 3), is also moved in direction A. Movement of the first articulation link 120 in direction A effects pivotal movement of the articulation member 123 which causes movement of the second articulation link 122 in the direction of arrow B. Movement of the second articulation link 122 in direction of arrow B causes movement of cartridge channel 140b in the direction of arrow B. As discussed above, the distal ends of cartridge channels 140a and 140b are connected to opposite sides of the pivot member 157. As the cartridge channels 140a and 140b are moved in opposite directions, the pivot member 157 is pivoted about the pivot pin 170 to pivot the tool assembly 114 in relation to shaft portion 112 such that the longitudinal axis of the tool assembly 114 is offset from the longitudinal axis of the shaft portion 112. It is noted that the cartridge channels 140a and 140b, the firing cams 138a and 138b and the distal drive members 136a and 136b are all formed of a resilient material such as spring steel to facilitate movement about the axis of articulation to an articulated position.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A cartridge assembly comprising:
   a cartridge body defining a longitudinal axis and having a distal portion and first and second spaced legs extending proximally from the distal portion, each of the first and second spaced legs defining a plurality of spaced notches, each of the spaced notches being fixed in relation to the distal portion of the cartridge body; and
   a plurality of staples, each of the plurality of staples including a backspan defining a transverse axis that is transverse to the longitudinal axis and having a first end and a second end, a first leg supported on the first end of the backspan, and a second leg supported on a second end of the backspan, each of the first and second legs being U-shaped and including a proximal leg portion and a distal leg portion, wherein the backspan of each of the plurality of staples is rotatably supported about the transverse axis in a respective laterally aligned notch defined in one of the first and second legs of the cartridge body.

2. The cartridge assembly of claim 1, wherein the proximal leg portions of the first and second legs of each of the plurality of staples are connected to the backspan.

3. The cartridge assembly of claim 2, wherein the distal leg portions of each of the plurality of staples include a tip configured to penetrate tissue.

4. The cartridge assembly of claim 3, wherein the tip of each of the distal leg portions of each of the plurality of staples is tapered.

5. The cartridge assembly of claim 1, wherein the distal leg portions of the first and second legs of each of the plurality of staples is curved and extends towards the backspan.

6. The cartridge assembly of claim 1, wherein each of the first and second legs of each of the plurality of staples define a longitudinal axis and the backspan defines a longitudinal axis, wherein the longitudinal axis of the backspan is perpendicular to the longitudinal axes of the first and second legs.

7. The cartridge assembly of claim 1, wherein each of the notches of the first and second spaced legs of the cartridge body defines a wide mouth configured to receive the backspan of one of the plurality of staples.

8. The cartridge assembly of claim 7, wherein each of the notches of the first and second spaced legs of the cartridge body defines a cylindrical slot that communicates with the wide mouth, the cylindrical slot configured to receive and pivotably support the backspan of a respective one of the plurality of staples.

9. The cartridge assembly of claim 1, wherein the first leg of each of the plurality of staples is positioned on an outer surface of one of the first and second legs of the cartridge body and the second leg of each of the plurality of staples is positioned on an inner surface of the one of the first and second legs of the cartridge body.

10. The cartridge assembly of claim 1, wherein the distal portion of the cartridge body is tapered downwardly in a distal direction.

11. The cartridge assembly of claim 10, wherein the cartridge body includes a plurality of fingers that extend proximally from the distal portion of the cartridge body between and on each side of the first and second spaced legs of the cartridge body.

12. The cartridge assembly of claim 1, wherein each of the first and second spaced legs of the cartridge body includes dimples associated with each of the notches, the dimples being positioned to support the first and second legs of each of the plurality of staples.

13. The cartridge assembly of claim 1, wherein each of the spaced notches in each of the first and second spaced legs receive the backspan of a respective one of the plurality of staples.

* * * * *